US012688466B1

(12) United States Patent
Puranik et al.

(10) Patent No.: US 12,688,466 B1
(45) Date of Patent: Jul. 21, 2026

(54) APPARATUS AND METHOD FOR IMPROVING FUNCTIONING OF A VALIDATED MACHINE-LEARNING MODEL

(71) Applicant: Anumana, Inc., Cambridge, MA (US)

(72) Inventors: Arjun Puranik, San Jose, CA (US); Nikhil Sachdeva, Murugeshpallya (IN); Shashi Kant, Bengaluru (IN); Rakesh Barve, Bengaluru (IN); Colin Pawlowski, Cambridge, MA (US)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 19/184,323

(22) Filed: Apr. 21, 2025

(51) Int. Cl.
| | |
|---|---|
| *G06F 17/00* | (2019.01) |
| *G06N 20/00* | (2019.01) |
| *G16H 50/20* | (2018.01) |

(52) U.S. Cl.
CPC ............. *G06N 20/00* (2019.01); *G16H 50/20* (2018.01)

(58) Field of Classification Search
CPC ............................... G06N 20/00; G16H 50/20
See application file for complete search history.

(56) References Cited

U.S. PATENT DOCUMENTS

| | | | | |
|---|---|---|---|---|
| 10,599,984 | B1 | 3/2020 | Wubbels et al. | |
| 10,810,512 | B1 | 10/2020 | Wubbels et al. | |
| 11,610,152 | B2 | 3/2023 | Edgar | |
| 12,033,051 | B2 * | 7/2024 | Blake | A61B 5/367 |
| 12,176,107 | B2 * | 12/2024 | Nair | G16H 50/30 |

| | | | | |
|---|---|---|---|---|
| 2018/0018579 | A1 * | 1/2018 | Xu | G06N 20/20 |
| 2020/0311608 | A1 * | 10/2020 | Xu | G06F 16/211 |
| 2021/0193291 | A1 * | 6/2021 | Blake | G16H 50/50 |
| 2023/0352146 | A1 * | 11/2023 | De Oliveira Correa | ..................... |
| | | | | G16H 50/30 |
| 2024/0062906 | A1 * | 2/2024 | Wipperman | G06N 3/09 |
| 2024/0315632 | A1 * | 9/2024 | de Bie | A61B 5/361 |

FOREIGN PATENT DOCUMENTS

| | | |
|---|---|---|
| IN | 202441044019 A | 6/2024 |
| WO | 2024236393 A1 | 11/2024 |
| WO | 2025012347 A | 1/2025 |

OTHER PUBLICATIONS

Igiri et al; Comparative Analysis of Supervised Machine Learning Algorithms for ECG Arrhythmia Detection using Small Dataset; "International Journal of Computer Science and Mathematical Theory (IJCSMT) vol. 9. No. 4 2023".

* cited by examiner

*Primary Examiner* — Greta L Robinson
(74) *Attorney, Agent, or Firm* — CALDWELL LLC

(57) ABSTRACT

An apparatus and method for improving functioning of a validated machine-learning model are disclosed. The apparatus includes a computing device having a processor and a memory, the memory containing instructions that, when run, configure the processor to receive a validated machine-learning model that has been trained on a validated training set, wherein the validated machine-learning model includes a first form accuracy metric, receive a paired data set including a plurality of data pairs of first form data paired with second form data and determine that a second form accuracy metric exceeds an accuracy threshold as a function of comparison of a paired output for each data pair of a plurality of data pairs and the first form accuracy metric.

16 Claims, 15 Drawing Sheets

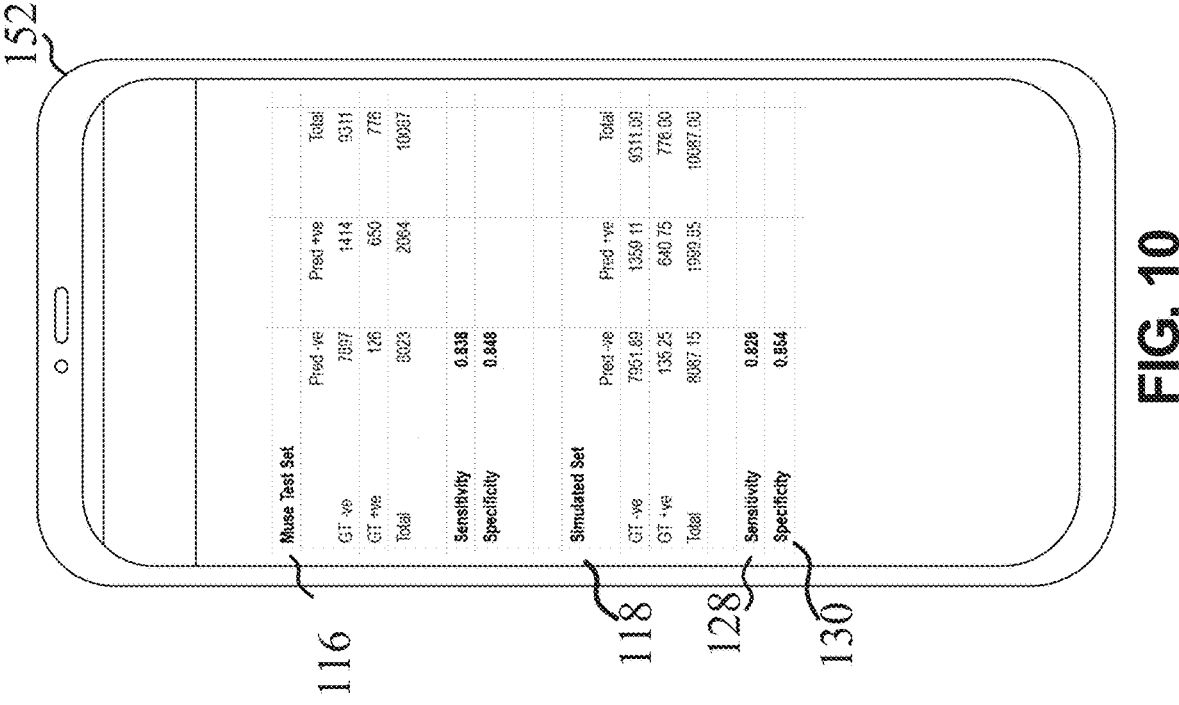
FIG. 10

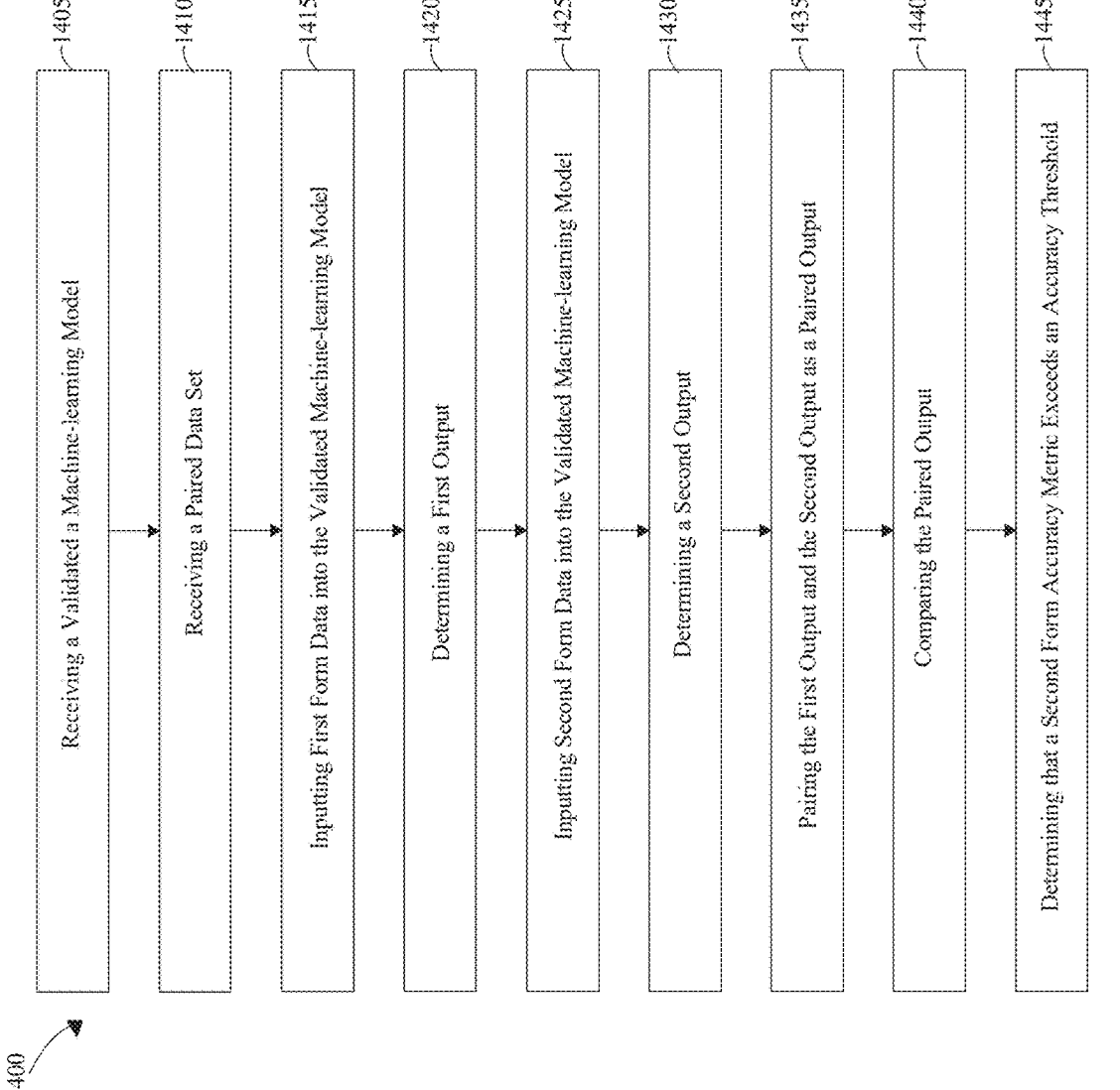

1405 — Receiving a Validated a Machine-learning Model

1410 — Receiving a Paired Data Set

1415 — Inputting First Form Data into the Validated Machine-learning Model

1420 — Determining a First Output

1425 — Inputting Second Form Data into the Validated Machine-learning Model

1430 — Determining a Second Output

1435 — Pairing the First Output and the Second Output as a Paired Output

1440 — Comparing the Paired Output

1445 — Determining that a Second Form Accuracy Metric Exceeds an Accuracy Threshold

APPARATUS AND METHOD FOR IMPROVING FUNCTIONING OF A VALIDATED MACHINE-LEARNING MODEL

FIELD OF THE INVENTION

The present invention generally relates to the field of artificial intelligence. In particular, the present invention is directed to an apparatus and method for improving functioning of a validated machine-learning model.

BACKGROUND

Machine-learning models have become integral to Software as a Medical Device (SaMD) applications, where they are used to analyze physiological data and generate diagnostic outputs. These models rely on large, well-curated datasets to learn patterns, make predictions, or classify data with high accuracy. However, a key challenge in deploying SaMD is ensuring that a machine-learning model validated on one dataset maintains equivalent or superior performance when applied to transformed versions of the data, especially when ground-truth information is unavailable for the transformed dataset. The model may need to process data obtained from different devices, transformed through alternative preprocessing techniques, or acquired under different conditions. This raises concerns about whether the model will maintain equivalent or superior performance across these variations.

For real-world deployment, the model may need to process transformed versions of this dataset, such as data captured by different medical devices or preprocessed using alternative algorithms. For example, a machine-learning model may have been validated on a test set, where clinical outcomes and performance metrics such as sensitivity and specificity are well established. If the model is later applied to a second data set, it becomes necessary to assess whether the model's performance remains equivalent, even though ground-truth labels for the second data set in the same clinical validation set may not be available. This challenge underscores the shortcomings of the existing technology to infer model performance on transformed datasets without direct access to ground-truth information.

SUMMARY OF THE DISCLOSURE

In an aspect, apparatus for improving functioning of a validated machine-learning model is disclosed. The apparatus includes a computing device having a processor and a memory, the memory containing instructions that, when run, configure the processor to receive a validated machine-learning model that has been trained on a validated training set including historical first form data correlated to historical ground truth data, wherein the validated machine-learning model comprises a first form accuracy metric, receive a paired data set including a plurality of data pairs of first form data paired with second form data, for each data pair of the plurality of data pairs, input the first form data into the validated machine-learning model, determine, using the validated machine-learning model, a first output as a function of the first form data, input the second form data into the validated machine-learning model, determine, using the validated machine-learning model, a second output as a function of the second form data, pair the first output and the second output as a paired output and compare the paired output by comparing the first output to the second output and determine that a second form accuracy metric exceeds an accuracy threshold as a function of the comparison of the paired output for each data pair of the plurality of data pairs and the first form accuracy metric.

In another aspect, a method for improving functioning of a validated machine-learning model is disclosed. The method includes receiving, using a processor, a validated machine-learning model that has been trained on a validated training set comprising historical first form data correlated to historical ground truth data, wherein the validated machine-learning model includes a first form accuracy metric, receiving, using the processor, a paired data set including a plurality of data pairs of first form data paired with second form data, inputting, using the processor, the first form data into the validated machine-learning model for each data pair of the plurality of data pairs, determining, using the processor and the validated machine-learning model, a first output as a function of the first form data for each data pair of the plurality of data pairs, inputting, using the processor, the second form data into the validated machine-learning model for each data pair of the plurality of data pairs, determining, using the processor and the validated machine-learning model, a second output as a function of the second form data for each data pair of the plurality of data pairs, pairing, using the processor, the first output and the second output as a paired output for each data pair of the plurality of data pairs, comparing, using the processor, the paired output by comparing the first output to the second output and determining, using the processor, that a second form accuracy metric exceeds an accuracy threshold as a function of the comparison of the paired output for each data pair of the plurality of data pairs and the first form accuracy metric.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 10 illustrates an exemplary user interface on a remote device;

FIG. 14 illustrates a flow diagram of an exemplary method for improving functioning of a validated machine-learning model.

DETAILED DESCRIPTION

At a high level, aspects of the present disclosure are directed to apparatuses and methods for improving functioning of a validated machine-learning model. The apparatus includes a computing device having a processor and a memory, the memory containing instructions that, when run, configure the processor to receive a validated machine-learning model that has been trained on a validated training set including historical first form data correlated to historical ground truth data, wherein the validated machine-learning model comprises a first form accuracy metric, receive a paired data set including a plurality of data pairs of first form data paired with second form data, for each data pair of the plurality of data pairs, input the first form data into the validated machine-learning model, determine, using the validated machine-learning model, a first output as a function of the first form data, input the second form data into the validated machine-learning model, determine, using the validated machine-learning model, a second output as a function of the second form data, pair the first output and the second output as a paired output and compare the paired output by comparing the first output to the second output and determine that a second form accuracy metric exceeds an accuracy threshold as a function of the comparison of the paired output for each data pair of the plurality of data pairs and the first form accuracy metric. Exemplary embodiments illustrating aspects of the present disclosure are described below in the context of several specific examples.

Figure 1:
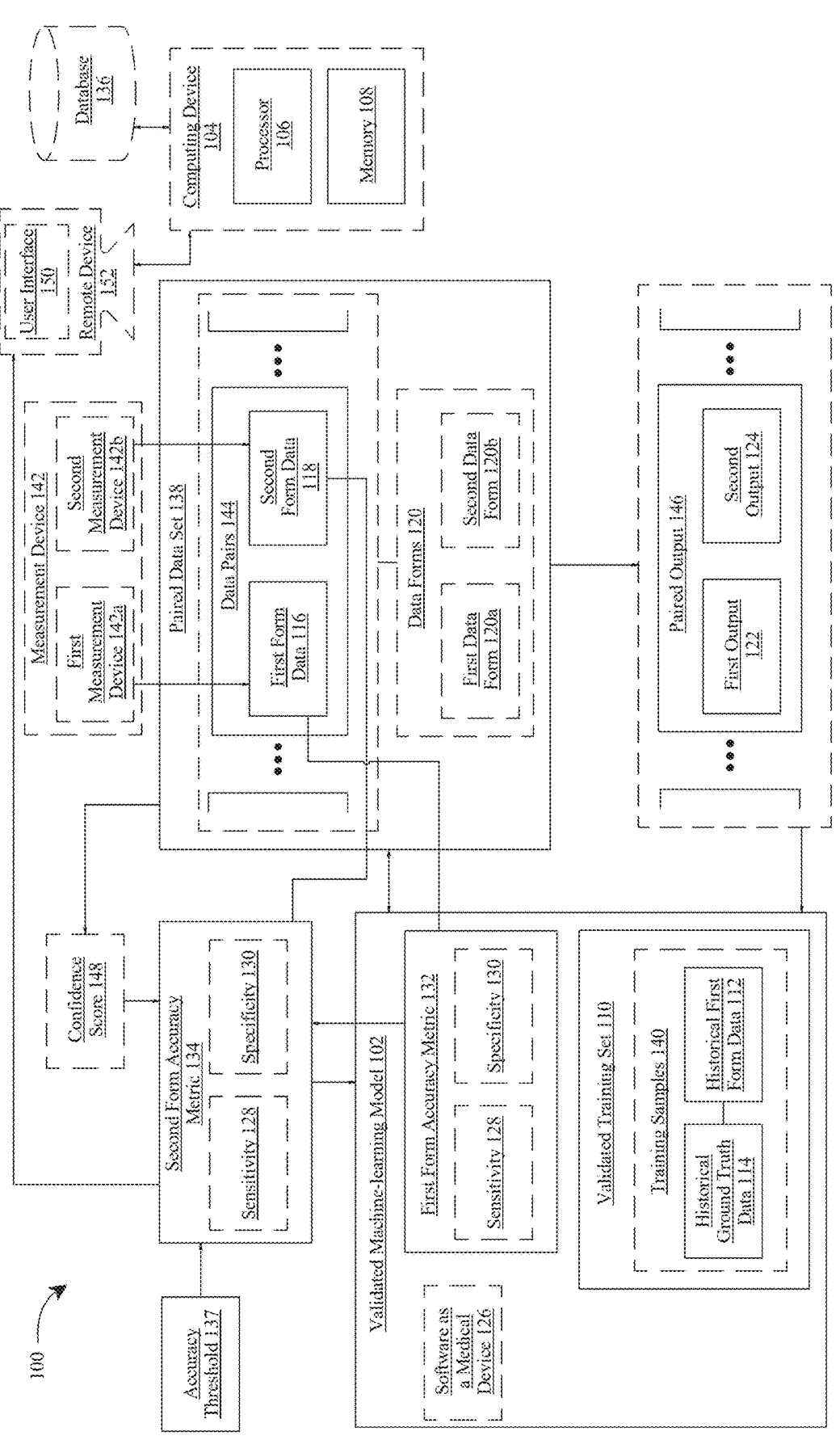
FIG. 1 illustrates a block diagram of an exemplary apparatus for improving functioning of a validated machine-learning model.

Referring now to FIG. 1, an exemplary embodiment of an apparatus 100 for improving functioning of a validated machine-learning model 102 is illustrated. Apparatus 100 includes a computing device 104. Computing device 104 includes at least a processor 106. Processor 106 may include, without limitation, any processor described in this disclosure. Processor 106 may be included in a computing device 104. Processor 106 may include any computing device as described in this disclosure, including without limitation a microcontroller, microprocessor, digital signal processor (DSP) and/or system on a chip (SoC) as described in this disclosure. Processor 106 may include, be included in, and/or communicate with a mobile device such as a mobile telephone or smartphone. Processor 106 may include a single computing device operating independently, or may include two or more computing device operating in concert, in parallel, sequentially or the like; two or more computing devices may be included together in a single computing device or in two or more computing devices. Processor 106 may interface or communicate with one or more additional devices as described below in further detail via a network interface device. Network interface device may be utilized for connecting processor 106 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 106 may include but is not limited to, for example, a computing device or cluster of computing devices in a first location and a second computing device or cluster of computing devices in a second location. Processor 106 may include one or more computing devices dedicated to data storage, security, distribution of traffic for load balancing, and the like. Processor 106 may distribute one or more computing tasks as described below across a plurality of computing devices of computing device, which may operate in parallel, in series, redundantly, or in any other manner used for distribution of tasks or memory between computing devices. Processor 106 may be implemented, as a non-limiting example, using a "shared nothing" architecture.

With continued reference to FIG. 1, processor 106 may be designed and/or configured to perform any method, method step, or sequence of method steps in any embodiment described in this disclosure, in any order and with any degree of repetition. For instance, processor 106 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 106 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, apparatus 100 includes a memory 108 communicatively connected to processor 106. For the purposes of this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, memory 108 contains instructions that, when run, configure processor 106 to receive a validated machine-learning model 102 that has been trained on a validated training set 110 including historical first form data 112 correlated to historical ground truth data 114. For the purposes of this disclosure, "historical first form data" is first form data that is previously used or generated. The first form data 116 disclosed herein is further described in detail below. For the purposes of this disclosure, "historical ground truth data" is ground truth data that is previously used or generated. The historical ground truth data 114 disclosed herein is further described in detail below. As used in this disclosure, a "validated training set" is a training data set that correlates data to ground truth data. In some cases, validated training set 110 may include data (e.g., first form data 116 and/or second form data 118) of a particular form (e.g., a plurality of data forms 120 described in detail below) correlated to ground truth data. As used in this disclosure, "ground truth data" is data that is known or believed to be true. As a non-limiting example, ground truth data may include any predictions related to raw data. For example, and without limitation, if first form data 116 is raw electrocardiogram (ECG) data, ground truth data may be left ventricular ejection fraction data. For example, and without limitation, ground truth data may include diagnosis of coronary artery disease, arrhythmias, heart failure, congenital heart defects, and the like. In some cases, ground truth data may be used to determine an accuracy metric of a machine-learning model. For instance, without limitation, by using model input data (e.g., first form data 116 and/or second form data 118) paired with ground truth data and comparing resulting model output data (e.g., first output 122 and/or second output 124 described in detail below) and the ground truth data.

With continued reference to FIG. 1, as used in this disclosure, a "validated machine-learning model" is a machine-learning model that has been tested to confirm its accuracy. In some embodiments, validated machine-learning model may have a known accuracy metric. In some embodiments, validated machine-learning model 102 may be consistent with any machine-learning model described in this disclosure. In some embodiments, validated machine-learning model 102 may include a software as a medical device (SaMD) 126. For the purposes of this disclosure, a "software as a medical device" is a software that is designed to be used for one or more medical purposes without being part of a physical medical device. In a non-limiting example, SaMD 126 may be capable of performing various functions. As a non-limiting example, SaMD 126 may be configured for diagnosis, treatment planning, monitoring, or providing recommendations for medical conditions or diseases. In some embodiments, SaMD 126 may include software applications that analyze physiological data (e.g., first form data 116 and/or second form data 118); for instance, and without limitation, ECG signals, medical imaging (e.g., X-rays, CT scans, MRIs), or laboratory results, to provide diagnostic outputs or treatment recommendations (e.g., first output 122, second output 124 and/or ground truth data). In some embodiments, SaMD 126 may interface with other medical devices.

With continued reference to FIG. 1, validated machine-learning model 102 may be consistent with any machine-learning models described in U.S. Nonprovisional patent application Ser. No. 16/754,007, filed on Oct. 22, 2024, entitled "ECG-BASED CARDIAC EJECTION-FRACTION SCREENING," U.S. Nonprovisional patent application Ser. No. 17/275,276, filed on Mar. 11, 2021, entitled "NEURAL NETWORKS FOR ATRIAL FIBRILLATION SCREENING," U.S. Nonprovisional patent application Ser. No. 18/151,673, filed on Jan. 9, 2023, entitled "NONINVASIVE METHODS FOR QUANTIFYING AND MONITORING LIVER DISEASE SEVERITY," U.S. Nonprovisional patent application Ser. No. 18/642,200, filed on Apr. 22, 2024, entitled "SYSTEM AND A METHOD FOR SCREENING FOR CARDIAC AMYLOIDOSIS BY ELECTROCARDIOGRAPHY," U.S. Nonprovisional patent application Ser. No. 18/642,012, filed on Apr. 22, 2024, entitled "SYSTEM AND A METHOD FOR ELECTRO-CARDIOGRAPHIC PREDICTION OF COMPUTED TOMOGRAPHY-BASED HIGH CORONARY CALCIUM SCORE (CAC)," U.S. Nonprovisional patent application Ser. No. 18/648,292, filed on Apr. 26, 2024, entitled "METHOD AND AN APPARATUS FOR DETECTING A LEVEL OF CARDIOVASCULAR DISEASE," U.S. Nonprovisional patent application Ser. No. 18/440,414, filed on Feb. 13, 2024, entitled "MACHINE-LEARNING FOR PROCESSING LEAD-INVARIANT ELECTROCARDIOGRAM INPUTS," U.S. Nonprovisional patent application Ser. No. 16/960,236, filed on Jul. 6, 2020, entitled "ECG-BASED AGE AND SEX ESTIMATION," U.S. Nonprovisional patent application Ser. No. 13/810,064, filed on Mar. 29, 2013, entitled "NON-INVASIVE MONITORING OF PHYSIOLOGICAL CONDITIONS," U.S. Nonprovisional patent application Ser. No. 15/778,405, filed on May 23, 2018, entitled "PROCESSING PHYSIOLOGICAL ELECTRICAL DATA FOR ANALYTE ASSESSMENTS," U.S. Nonprovisional patent application Ser. No. 15/842,419, filed on Dec. 14, 2017, entitled "SYSTEMS AND METHODS OF ANALYTE MEASUREMENT ANALYSIS," U.S. Nonprovisional patent application Ser. No. 18/517,640, filed on Nov. 22, 2023, entitled "SYSTEM AND APPARATUS FOR GENERATING IMAGING INFORMATION BASED ON AT LEAST A SIGNAL," U.S. Nonprovisional patent application Ser. No. 18/229,033, filed on Aug. 1, 2023, entitled "APPARATUS AND A METHOD FOR THE IMPROVEMENT OF ELECTROCARDIOGRAM VISUALIZATION," U.S. Nonprovisional patent application Ser. No. 17/500,287, filed on Oct. 13, 2021, entitled "NONINVASIVE METHODS FOR DETECTION OF PULMONARY HYPERTENSION," U.S. Nonprovisional patent application Ser. No. 17/552,246, filed on Dec. 15, 2021, entitled "SYSTEMS AND METHODS FOR DIAGNOSING A HEALTH CONDITION BASED ON PATIENT TIME SERIES DATA," each of which is incorporated herein by reference in its entirety.

With continued reference to FIG. 1, as used in this disclosure, an "accuracy metric" is a measure of output of machine-learning model's relative ground truth. In some cases, accuracy metric may include one or both of sensitivity 128 and specificity 130. In some embodiments, the known accuracy metric may be form-specific. As a non-limiting example, the accuracy metric (first form accuracy metric 132 and/or second form accuracy metric 134 described in detail below) may be reflective of model accuracy when data of a particular data form 120 is input into validated machine-learning model 102. For the purposes of this disclosure, a "data form" is a specific format, structure, or representation of data. In some embodiments, data form 120 may include a way data is encoded, organized, or visualized and can vary depending on the source, transformation, or intended application. As a non-limiting example, data form 120 may include numerical vectors, time-series signals, tabular data, images, audio files, or textual representations. For example, and without limitation, data form 120 may include signals, waveforms, and the like. In some embodiments, data form 120 may include a modality. For the purposes of this disclosure, a "modality" is a method, system, or type of measurement used to acquire or represent data. In some embodiments, modality may represent a source and nature of first form data 116 and/or second form data 118. As a non-limiting example, a modality may include electrocardiography (ECG) for capturing electrical activity of the heart, imaging techniques, and the like. For example, and without limitation, modality may include magnetic resonance imaging (MRI), computed tomography (CT), X-rays, echocardiography, or the like. For example, and without limitation, data form 120 may include 12-lead XML signal, digital vector pdf, image, lower lead, and the like.

With continued reference to FIG. 1, for the purposes of this disclosure, "sensitivity" is a measure of an ability of a model to correctly identify positive cases. In some embodiments, sensitivity 128 may be mathematically expressed as a proportion of true positives (e.g., cases correctly identified as positive) out of a total number of actual positives, and may be given by a formula:

$$Sensitivity = \frac{Number\ of\ True\ Positives}{Number\ of\ True\ Positives + Number\ of\ False\ Negatives}.$$

For the purposes of this disclosure, "specificity" is a measure of a model's ability to correctly identify true negative cases. In some embodiments, specificity 130 may be mathematically expressed as a proportion of true negatives (e.g., cases correctly identified as negative) out of a total number of actual negatives, and may be given by the formula:

$$Specificity = \frac{Number\ of\ True\ Negatives}{Number\ of\ True\ Negatives + Number\ of\ False\ Posiitives}.$$

The sensitivity 128 and the specificity 130 described herein are further described in detail below.

With continued reference to FIG. 1, in some embodiments, processor 106 may be configured to generate a validated training set 110. In some embodiments, validated training set 110 may be stored in database 136. In some embodiments, validated training set 110 may be received from one or more users, database 136, external computing devices, and/or previous iterations of processing. As a non-limiting example, validated training set 110 may include instructions from a user, who may be an expert user, a past user in embodiments disclosed herein, or the like, which may be stored in memory and/or stored in database 136, where the instructions may include labeling of training examples. In some embodiments, validated training set 110 may be updated iteratively on a feedback loop. In some embodiments, determining that second form accuracy metric 134 exceeds accuracy threshold 137 may include updating validated machine-learning model 102 using second form accuracy metric 134. As a non-limiting example, processor 106 may update validated training set 110 iteratively through a feedback loop as a function of first form data 116, second form data 118, first output 122, second output 124, first form accuracy metric 132, second form accuracy metric 134, accuracy threshold 137, or the like. The first output 122 and the second output 124 described herein are further described in detail below. In some embodiments, updating validated machine-learning model 102 and/or validated training set 110 may include adding correlations between second form data 118 and second output 124 to validated training set 110 as a function of second form accuracy metric 134. For example, and without limitation, if second form accuracy metric 134 is determined to exceed accuracy threshold 137, then second form data 118, second output 124 and their correlation may be added to validated training set 110. In some embodiments, processor 106 may be configured to generate a validated machine-learning model 102. In a non-limiting example, generating validated machine-learning model 102 may include training, retraining, or fine-tuning validated machine-learning model 102 using validated training set 110 or updated validated training set 110. In some embodiments, processor 106 may be configured to determine first output 122 and/or second output 124 using validated machine-learning model 102 (i.e. trained or updated validated machine-learning model 102).

With continued reference to FIG. 1, in some embodiments, apparatus 100 may include a database 136. As used in this disclosure, "database" is a data structure configured to store data associated with a paired data set. In one or more embodiments, database 136 may include inputted or calculated information and datum related to a paired data set 138. In some embodiments, a datum history may be stored in database 136. As a non-limiting example, the datum history may include real-time and/or previous inputted data related to paired data set 138. As a non-limiting example, database 136 may include instructions from a user, who may be an expert user, a past user in embodiments disclosed herein, or the like, where the instructions may include examples of the data related to paired data set 138.

With continued reference to FIG. 1, in some embodiments, processor 106 may be communicatively connected with database 136. For example, and without limitation, in some cases, database 136 may be local to processor 106. In another example, and without limitation, database 136 may be remote to processor 106 and communicative with processor 106 by way of one or more networks. The network may include, but is not limited to, a cloud network, a mesh network, and the like. By way of example, a "cloud-based" system can refer to a system which includes software and/or data which is stored, managed, and/or processed on a network of remote servers hosted in the "cloud," e.g., via the Internet, rather than on local severs or personal computers. A "mesh network" as used in this disclosure is a local network topology in which the infrastructure processor 106 connect directly, dynamically, and non-hierarchically to as many other computing devices as possible. A "network topology" as used in this disclosure is an arrangement of elements of a communication network. The network may use an immutable sequential listing to securely store database 136. An "immutable sequential listing," as used in this disclosure, is a data structure that places data entries in a fixed sequential arrangement, such as a temporal sequence of entries and/or blocks thereof, where the sequential arrangement, once established, cannot be altered or reordered. An immutable sequential listing may be, include and/or implement an immutable ledger, where data entries that have been posted to the immutable sequential listing cannot be altered.

With continued reference to FIG. 1, in some embodiments, database 136 may be implemented, without limitation, as a relational database, a key-value retrieval database such as a NOSQL database, or any other format or structure for use as a database that a person skilled in the art would recognize as suitable upon review of the entirety of this disclosure. Database may alternatively or additionally be implemented using a distributed data storage protocol and/or data structure, such as a distributed hash table or the like. Database may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

With continued reference to FIG. 1, in some embodiments, receiving validated machine-learning model 102 may include selecting training samples 140 from a plurality of sets of a validated training set 110 as a function of a data form 120 of one or both of first form data 116 and second form data 118 and training the validated machine-learning model 102 using the selected training samples 140. For the purposes of this disclosure, a "training sample" is a data instance from a validated training set. In some embodiments, training samples 140 may include input data (e.g., historical first form data 112 with different data form 120) and corresponding ground-truth labels. In some embodiments, selecting training samples 140 as a function of a data form 120 may include filtering training samples 140 in a validated training set 110 by data modality (data form 120) to use training samples 140 that match a specific data form 120 or representation of first form data 116 and/or second form data 118 expected by validated machine-learning model 102. For example, and without limitation, when training validated machine-learning model 102 to process first form data 116 and/or second form data 118 as digital vectors, training samples 140 may be filtered to include only vectorized representations from validated training set 110. For example, and without limitation, when validated machine-learning model 102 is trained to handle first form data 116 and/or second form data 118 as images, training samples 140 may be filtered to include image-based data forms. In some embodiments, receiving validated machine-learning model

102 may include selecting training samples 140 from a plurality of sets of a validated training set 110 as a function of modality of data form 120 of one or both of first form data 116 and second form data 118 and training the validated machine-learning model 102 using the selected training samples 140. In a non-limiting example, selecting training samples 140 based on modality may include identifying training samples 140 that correspond to a specific type of data generated by a particular measurement device 142 or method. For example, and without limitation, when training validated machine-learning model 102 to process ECG signals, training samples 140 may include time-series data or digital vectors representing electrical activity of a heart. For example, and without limitation, when training validated machine-learning model 102 for MRI or CT modalities, training samples 140 may include high-resolution grayscale or color images. In some embodiments, selecting training samples 140 may include preprocessing training samples 140 for compatibility with validated machine-learning model 102. As a non-limiting example, preprocessing training samples 140 may include normalizing signal amplitudes, resizing images, or aligning time-series data to ensure uniformity across validated training set 110.

With continued reference to FIG. 1, in some embodiments, first form data 116 and/or second form data 118 may be classified to a subject cohort using a cohort classifier. Cohort classifier may be consistent with any classifier discussed in this disclosure. Cohort classifier may be trained on cohort training data, wherein the cohort training data may include first form data 116 and/or second form data 118 correlated to subject cohorts. In some embodiments, a subject, first form data 116 and/or second form data 118 may be classified to a subject cohort and processor 106 may determine first output 122 and/or second output 124 based on the subject cohort using a machine-learning module as described in detail with respect to FIG. 11 and the resulting output may be used to update validated training set 110. In some embodiments, generating training data and training machine-learning models may be simultaneous.

With continued reference to FIG. 1, validated machine-learning model 102 includes a first form accuracy metric 132. For the purposes of this disclosure, a "first form accuracy metric" is a measure used to evaluate a performance of a validated machine-learning model when processing first form data. In some embodiments, first accuracy metric 132 may be form specific, wherein the first form accuracy metric 132 may be reflective of model accuracy when the first form data 116 in a particular data form 120 is input into validated machine-learning model 102. In a non-limiting example, first form accuracy metric 132 may reflect an ability of a validated machine-learning model 102 to generate correct or true outputs or classifications based on first form data 116. In some embodiments, first form accuracy metric 132 may include one or both of sensitivity 128 and specificity 130. As a non-limiting example, first form accuracy metric 132 may include sensitivity 128, specificity 130, precision, recall, F1-score, or overall accuracy, or the like. In some embodiments, first form accuracy metric 132 may be stored in database 136 and processor 106 may retrieve first form accuracy metric 132 from database 136. In some embodiments, first form accuracy metric 132 may be manually input by a user.

With continued reference to FIG. 1, memory 108 contains instructions that, when run, configure processor 106 to receive a paired data set 138 including a plurality of data pairs 144 of first form data 116 paired with second form data 118. For the purposes of this disclosure, a "paired data set" is a collection of data composed of a plurality of data pairs. For the purposes of this disclosure, a "data pair" is a set of two associated data points. For the purposes of this disclosure, "first form data" is data originating from a first measurement device. As a non-limiting example, first form data 116 may include any raw data generated by first measurement device 142a. For example, and without limitation, first form data 116 may include ECG signal (ECG data), echocardiogram (echo) signal, magnetic resonance image (MRI) images, computed tomography (CT) images, X-ray images, and the like. For the purposes of this disclosure, "electrocardiogram data" is information related to the electrical activity of the heart over a period of time. In one or more embodiments, ECG data may include a matrix having a plurality of electrocardiogram signals and/or associated time variables. A "matrix" for the purposes of this disclosure is an array of numbers or characters arranged in rows or columns which are used to represent an object or properties of the object. For example, and without limitation, a matrix may be used to describe linear equations, differential equations, in a two-dimensional format. In another non limiting example, a matrix may be used to create graphs based on data points, generate statistical models and the like. In one or more embodiments, matrix may include a plurality of electrocardiogram signals associated with a plurality of time variables. As used in the current disclosure, a "electrocardiogram signal" is a signal representative of electrical activity of heart. The ECG signal may consist of several distinct waves and intervals, each representing a different phase of the cardiac cycle. These waves may include the P-wave, QRS complex, T wave, U wave, and the like. The P-wave may represent atrial depolarization (contraction) as the electrical impulse spreads through the atria. The QRS complex may represent ventricular depolarization (contraction) as the electrical impulse spreads through the ventricles. The QRS complex may include three waves: Q wave, R wave, and S wave. The T-wave may represent ventricular repolarization (recovery) as the ventricles prepare for the next contraction. The U-wave may sometimes be present after the T wave, it represents repolarization of the Purkinje fibers. The intervals between these waves may provide information about the duration and regularity of various phases of the cardiac cycle. The ECG signal may help diagnose various heart conditions, such as arrhythmias, myocardial infarction (heart attack), conduction abnormalities, and electrolyte imbalances. In one or more embodiments, ECG signals may be received by one or more electrodes connected to the skin of an individual. In one or more embodiments, ECG signals may represent depolarization and repolarization occurring in the heart. In one or more embodiments, ECG signals may be captured periodically. For example, and without limitation, every second, every millisecond and the like. For the purposes of this disclosure, "second form data" is data originating from a second measurement device. As a non-limiting example, second form data 118 may include any raw data generated by second measurement device 142b. For example, and without limitation, second form data 118 may include ECG signal (ECG data), echocardiogram (echo) signal, magnetic resonance image (MRI) images, computed tomography (CT) images, X-ray images, and the like.

With continued reference to FIG. 1, for the purposes of this disclosure, a "measurement device" is a device or system designed for capturing data. In a non-limiting example, measurement device 142 may be configured to capture data related to physiological, medical, or similar phenomena. For example, and without limitation, measurement device 142 may capture data (first form data 116 and/or second form data 118) related to electrocardiogram (ECG). As a non-limiting example, measurement device 142 may include any medical devices designed for capturing electrocardiographic or physiological data. For example, and without limitation, measurement device 142 may include a device that monitors electrical activity of the heart or other physiological signals. In some embodiments, first measurement device 142a and second measurement device 142b may capture same phenomena but generate an output in a different data form 120. In some embodiments, plurality of data pairs 144 may include measurements of a same phenomenon of a same subject obtained using two different measurement devices. For example, and without limitation, the phenomenon may be the electrical activity of the heart, and the subject may be a patient undergoing diagnostic evaluation. For the purposes of this disclosure, a "phenomenon" is any measurable event, condition, or property that can be observed, recorded, or quantified by a measurement device. A phenomenon may include physiological, biological, physical, or chemical characteristics or processes. As a non-limiting example, a phenomenon may include electrical activity of the heart, blood pressure, respiratory rate, body temperature, or chemical concentrations in blood or tissue. For the purposes of this disclosure, a "subject" is an individual, entity, or object from which measurements of a phenomenon are obtained. In some embodiments, a subject may be a human patient, an animal, or a non-living entity (e.g., a mechanical system, material, or environment) depending on the application of measurement devices. As a non-limiting example, a subject may include a patient undergoing diagnostic evaluation for medical conditions. In some embodiments, first form data 116 and second form data 118 may have different data forms 120 while the data of different data forms 120 need not have different substance. In a non-limiting example, first form data 116 originating from a first measurement device 142a may have a different data form 120 than second form data 118 originating from a second measurement device 142b, even if the two devices are measuring identical phenomena. For example, and without limitation, first form data 116 may include a first data form 120a and second form data 118 may include a second data form 120b.

With continued reference to FIG. 1, in some embodiments, receiving paired data set 138 may include transforming first form data 116 in a first data form 120a into a second data form 120b as a function of a transformation model. In some embodiments, receiving paired data set 138 may include transforming second form data 118 in a first data form 120a into a second data form 120b. For example, and without limitation, first data form 120a may include a vector representation of signal data, while second data form 120b may include image data generated from the vector representation. For example, and without limitation, first data form 120a may include image data, while second data form 120b may include a vector representation of the image data. In some embodiments, transforming first form data 116 and/or second form data 118 in a first data form 120a into a second data form 120b may include filtering, formatting, feature extraction, or visualization.

With continued reference to FIG. 1, for the purposes of this disclosure, a "transformation model" is a computational process, algorithm, or function that transforms data in a data form to another data form. As a non-limiting example, transformation model may be configured to transform first form data 116 in a first data form 120a into a second data form 120b. As another non-limiting example, transformation model may be configured to transform second form data 118 in a first data form 120*a* into a second data form 120*b*. In some embodiments, transformation model may include a feature fusing sub-neural network. For the purposes of this disclosure, a "feature fusing sub-neural network" is a neural network that fuses a feature of two different data. Different neural networks, e.g., neural networks with different parameter values, different model architectures, or both, may be used to process ECG data (e.g., first form data 116, second form data 118, and the like) in different formats (e.g., data forms 120), different length, or collected using different hardware devices or measurement devices 142. In some embodiments, transformation model may include a stack of one or more convolutional neural network layers and, in some cases, one or more non-linear activation layers that are collectively configured to process the neural network input to extract temporal features (e.g., rather than spatial features) of the input. The extracted temporal features from ECG data (e.g., first form data 116, second form data 118, and the like) collected using each single ECG lead may be then combined, e.g., by using a pooling layer, and processed by a sub-neural network to generate the neural network output. In this way, the neural network may be easily configurable to process ECG data collected using different hardware devices, measurement devices 142 (e.g., devices with different lead numbers, or in different time length). In some cases, transformation model may include a feature extraction sub-neural network that extract features of data (e.g., first form data 116, second form data 118, and the like). In some cases, the feature extraction sub-neural network may be fully convolutional, i.e., does not include any fully-connected layers that have a fixed number of connections between the neurons. This allows for transformation model to be able to accept ECG data in any of a variety of lengths. In some cases, the hardware agnostic neural network may be invariant to ECG lead direction. In a non-limiting example, suitable artificial neural networks may include a feedforward neural network, a radial basis function network, a self-organizing map, learning vector quantization, a recurrent neural network, a Hopfield network, a Boltzmann machine, an echo state network, long short term memory, a bi-directional recurrent neural network, a hierarchical recurrent neural network, a stochastic neural network, a modular neural network, an associative neural network, a deep neural network, a deep belief network, a convolutional neural networks, a convolutional deep belief network, a large memory storage and retrieval neural network, a deep Boltzmann machine, a deep stacking network, a tensor deep stacking network, a spike and slab restricted Boltzmann machine, a compound hierarchical-deep model, a deep coding network, a multilayer kernel machine, or a deep Q-network. Additional disclosure related to transformation model, feature extraction sub-neural network, and feature fusing sub-neural network may be found in U.S. Nonprovisional patent application Ser. No. 18/440,414, filed on Feb. 13, 2024, entitled "MACHINE-LEARNING FOR PROCESS-ING LEAD-INVARIANT ELECTROCARDIOGRAM INPUTS," the entirety of which is incorporated as a reference.

With continued reference to FIG. 1, in some embodiments, transformation model may include a signal conversion model. For the purposes of this disclosure, a "signal conversion model" is a computational process, algorithm, or function that converts a data signal from different data channels. For example, and without limitation, signal conversion model may be able to take a signal from one type of machine or measurement device 120 (e.g., a 12-lead ECG)

and estimate what the corresponding 6-lead ECG would look like and vice-versa. Training data that may be used to train the signal conversion model may include exemplary input data, such as without limitation, a first set of signals (first form data 116 in a first data form 120*a*), a second set of signals (second form data 118 in a second data form 120*a*), a filtered first set of signals (first form data 116 in a second data form 120*b*), a filtered second set of signals (second form data 118 in a second data form 120*a*), known electrical anomalies associated with desired channel selections, signals of desired channel configurations, predictions of signals of desired channel selections, and/or the like, where each such example may be correlated to additional exemplary output data such as, without limitation, a first set of signals, a second set of signals, a filtered first set of signals, a filtered second set of signals, known electrical anomalies associated with desired channel configurations, signals of desired channel configurations, predictions of signals of desired channel configurations, and/or the like. Training of the signal conversion model may take place either at apparatus 100 and/or remotely; in the latter case, the model may be deployed at or by apparatus 100 in any manner as described within this disclosure. Additionally, in some embodiments, the signal conversion model may be updated to apparatus 100, the model may be deployed at or by apparatus 100 in any manner as described in this disclosure. The signal conversion model may be deployed/instantiated once trained in any form as described within this disclosure. Feedback from the deployment of the signal conversion model may be turned into new training data, which may be stored either locally and/or transmitted to another device and used for retraining of the model. Retraining may be administered either remotely or at apparatus 100. Following the retraining of the ECG reading conversion model, redeployment/instantiation may be accomplished at or by apparatus 100 in any manner as described within this disclosure. Additional disclosure related to transformation model and a signal conversion model may be found in U.S. Nonprovisional patent application Ser. No. 18/648,250, filed on Apr. 26, 2024, entitled "APPARATUS (AND/OR METHOD) OF TRAINING A MACHINE-LEARNING MODEL TO GENERATE DETERMINATIONS USING MISMATCHED-CHANNEL SIGNALS," the entirety of which is incorporated as a reference.

With continued reference to FIG. 1, a "vector" as defined in this disclosure is a data structure that represents one or more a quantitative values and/or measures from a measurement device. Such vector and/or embedding may include and/or represent an element of a vector space; a vector may alternatively or additionally be represented as an element of a vector space, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. A vector may be represented as an n-tuple of values, where n is one or more values, as described in further detail below; a vector may alternatively or additionally be represented as an element of a vector space, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent, for instance as measured using cosine similarity as computed using a dot product of two vectors; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute 1 as derived using a Pythagorean norm:

$$l = \sqrt{\sum_{i=0}^{n} a_i^2},$$

where ai is attribute number i of the vector. Scaling and/or normalization may function to make vector comparison independent of absolute quantities of attributes, while preserving any dependency on similarity of attributes. A two-dimensional subspace of a vector space may be defined by any two orthogonal vectors contained within the vector space. Two-dimensional subspace of a vector space may be defined by any two orthogonal and/or linearly independent vectors contained within the vector space; similarly, an n-dimensional space may be defined by n vectors that are linearly independent and/or orthogonal contained within a vector space. A vector's "norm' is a scalar value, denoted ||a|| indicating the vector's length or size, and may be defined, as a non-limiting example, according to a Euclidean norm for an n-dimensional vector a as:

$$\|a\| = \sqrt{\sum_{i=0}^{n} a_i^2}$$

In an embodiment, and with continued reference to FIG. 1, each data points in first form data 116 and/or second form data 118 may be represented by a dimension of a vector space; as a non-limiting example, each element of a vector may include a number representing an enumeration of co-occurrences of physiological measurements represented by the vector with data point. Alternatively, or additionally, dimensions of vector space may not represent distinct data point, in which case elements of a vector representing a data point may have numerical values that together represent a geometrical relationship to a vector representing another data point or measurement, wherein the geometrical relationship represents and/or approximates a semantic relationship between the data points in first form data 116 and/or second form data 118. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below.

With continued reference to FIG. 1, any vectors as described herein may be scaled, such that each vector represents each attribute along an equivalent scale of values. In an embodiment associating first form data 116 and/or second form data 118 to one another as described above may include computing a degree of vector similarity between a vector representing each data points in first form data 116 and/or second form data 118 and a vector representing another data points in first form data 116 and/or second form data 118; vector similarity may be measured according to any norm for proximity and/or similarity of two vectors, including without limitation cosine similarity. As used in this disclosure, "cosine similarity" is a measure of similarity between two-non-zero vectors of a vector space, wherein determining the similarity includes determining the cosine of the angle between the two vectors. Cosine similarity may be computed as a function of using a dot product of the two vectors divided by the lengths of the two vectors, or the dot product of two normalized vectors. For instance, and without limitation, a cosine of 0° is 1, wherein it is less than 1 for any angle in the interval $(0,\pi)$ radians. Cosine similarity may be a judgment of orientation and not magnitude, wherein two vectors with the same orientation have a cosine similarity of 1, two vectors oriented at 90° relative to each other have a similarity of 0, and two vectors diametrically opposed have a similarity of −1, independent of their magnitude. As a non-limiting example, vectors may be considered similar if parallel to one another. As a further non-limiting example, vectors may be considered dissimilar if orthogonal to one another. As a further non-limiting example, vectors may be considered uncorrelated if opposite to one another. Additionally, or alternatively, degree of similarity may include any other geometric measure of distance between vectors.

With continued reference to FIG. 1, for each data pair 144 of a plurality of data pairs 144, processor 106 is configured to input first form data 116 into validated machine-learning model 102, determine, using the validated machine-learning model 102, a first output 122 as a function of the first form data 116. For the purposes of this disclosure, a "first output" is ground truth data that is generated based on first form data. As a non-limiting example, first output may be any predictions or diagnosis resulted by analyzing first form data 116. For example, and without limitation, first output 122 may include diagnosis of coronary artery disease, arrhythmias, heart failure, congenital heart defects, and the like based on ECG signal, echocardiogram (echo) signal, magnetic resonance image (MRI) images, computed tomography (CT) images, X-ray images, and the like. In some embodiments, first output 122 may be stored in database 136 and processor 106 may retrieve first output 122 from database 136. In some embodiments, user may manually input a first output 122.

With continued reference to FIG. 1, for each data pair 144 of a plurality of data pairs 144, processor 106 is configured to input second form data 118 into validated machine-learning model 102 and determine, using the validated machine-learning model 102, a second output 124 as a function of the second form data 118. For the purposes of this disclosure, a "second output" is ground truth data that is generated based on second from data. As a non-limiting example, second output may be any predictions or diagnosis resulted by analyzing second form data 118. For example, and without limitation, second output 124 may include diagnosis of coronary artery disease, arrhythmias, heart failure, congenital heart defects, and the like based on ECG signal, echocardiogram (echo) signal, magnetic resonance image (MRI) images, computed tomography (CT) images, X-ray images, and the like. In some embodiments, second output 124 may be stored in database 136 and processor 106 may retrieve second output 124 from database 136. In some embodiments, user may manually input a second output 124.

With continued reference to FIG. 1, for each data pair 144 of a plurality of data pairs 144, processor 106 is configured to pair a first output 122 and a second output 124 as a paired output 146 and compare the paired output 146 by comparing the first output 122 to the second output 124. For the purposes of this disclosure, a "paired output" is a combined set of a first output and a second output. In some embodiments, paired output 146 may be represented as a structured data object. As a non-limiting example, paired output 146 may include a table, list, matrix, or the like. In some embodiments, paired output 146 may be stored in database 136 and processor 106 may retrieve paired output 146 from database 136. In some embodiments, user may manually input paired output 146.

With continued reference to FIG. 1, for each data pair 144 of a plurality of data pairs 144, processor 106 is configured to determine that a second form accuracy metric 134 exceeds an accuracy threshold 137 as a function of comparison of paired output 146 for each data pair 144 of a plurality of data pairs 144 and first form accuracy metric 132. In some embodiments, the comparison may evaluate discrepancies between first output 122 and second output 124 for each data pair 144, quantifying the closeness of the outputs to derive sensitivity 128, specificity 130, or other accuracy metrics. In some embodiments, processor 106 may be configured to quantify mismatches between paired output 146. For instance, processor 106 may be configured to quantify where first output 122 indicates a positive classification, and second output 124 indicates a negative classification, or vice versa. In some embodiments, second form accuracy metric 134 may be calculated using statistical bounds derived from the discrepancies. In some embodiments, a Bayesian approach may be used to refine sensitivity 128 and specificity 130 for second form data 118 or second output 124. These methods of determining whether a second form accuracy metric 134 exceeds an accuracy threshold 137 are further described in detail below.

With continued reference to FIG. 1, for the purposes of this disclosure, a "second form accuracy metric" is a measure used to evaluate a performance of a validated machine-learning model when processing second form data. In some embodiments, second form accuracy metric 134 may be form specific, wherein the second form accuracy metric 134 may be reflective of model accuracy when the second form data 118 in a particular data form 120 is input into validated machine-learning model 102. In a non-limiting example, second form accuracy metric 134 may reflect an ability of a validated machine-learning model 102 to generate correct or true outputs or classifications based on second form data 118. In some embodiments, second form accuracy metric

134 may include one or both of sensitivity 128 and specificity 130. As a non-limiting example, second form accuracy metric 134 may include sensitivity 128, specificity 130, precision, recall, F1-score, or overall accuracy, or the like. In some embodiments, second form accuracy metric 134 may be stored in database 136 and processor 106 may retrieve second form accuracy metric 134 from database 136. In some embodiments, second form accuracy metric 134 may be manually input by a user.

With continued reference to FIG. 1, for the purposes of this disclosure, an "accuracy threshold" is a value that serves as a benchmark for evaluating a performance of a validated machine-learning model. In some embodiments, accuracy threshold 137 may be predefined. As a non-limiting example, processor 106 may retrieve accuracy threshold 137 from database 136. As another non-limiting example, user may manually input accuracy threshold 137. In some embodiments, processor 106 may dynamically determine accuracy threshold 137 as a function of first form data 116, second form data 118, first output 122, second output 124, first data form 120a, and/or the like. In some embodiments, accuracy threshold 137 may represent a minimum acceptable level of a second form accuracy metric 134 (e.g., sensitivity 128 and/or specificity 130) that validated machine-learning model 102 must meet or exceed. For example, and without limitation, accuracy threshold 137 may be a value between a range of 0 to 1.

With continued reference to FIG. 1, in some embodiments, determining that second form accuracy metric 134 exceeds accuracy threshold 137 may include generating a confidence score 148 for each data pair 144 of a plurality of data pairs 144 and determining that the second form accuracy metric 134 exceeds the accuracy threshold 137 as a function of the confidence score 148. In some embodiments, determining that second form accuracy metric 134 exceeds accuracy threshold 137 may include generating a confidence score 148 for paired output 146 of each data pair 144 of a plurality of data pairs 144. In some embodiments, determining that second form accuracy metric 134 exceeds accuracy threshold 137 may include generating a confidence score 148 as a function of a closeness of paired output 146 to the accuracy threshold 137. For the purposes of this disclosure, a "confidence score" is a score that quantifies the likelihood or certainty of the model's outputs for each data pair of a plurality of data pairs being correct. In some embodiments, confidence score 148 may include positive, negative, uncertain, strong positive, borderline positive, strong negative, borderline negative classification, and the like. In some embodiments, confidence score 148 may be a numerical value within a predefined range where higher values indicate greater confidence in the accuracy of an output of validated machine-learning model. As a non-limiting example, the predefined range may be between 0 to 1. In some embodiments, a confidence score 148 may be determined based on probability that an input data point (e.g., first output 122 and second output 124 of each data pair 144 of a plurality of data pairs 144) belongs to a specific class or category. For example, and without limitation, for a binary classification task, a confidence score of 0.9 for a "positive" classification may indicate that validated machine-learning model 102 predicts the positive class with 90% confidence. In some embodiments, processor 106 may be configured to classify outputs (e.g., first output 122 and second output 124 of each data pair 144 of a plurality of data pairs 144) as positive, negative, uncertain, strong positive, borderline positive, strong negative, borderline negative, and the like and aggregate confidence scores 148 to compute accuracy metrics (e.g., first form accuracy metric 132 and/or second form accuracy metric 134). For instance, and without limitation, in a paired data set 138 consisting of ECG signals transformed into two forms (first form data 116 and second form data XX), validated machine-learning model 102 may assign confidence scores 148 for detecting arrhythmias in both first and second outputs 124. Continuing the non-limiting example, confidence scores 148 may then be paired and compared to evaluate performance consistency across the data forms. In some embodiments, in multi-class classification tasks, confidence scores 148 for each class may indicate certainty of validated machine-learning model about its diagnosis (first output 122 and/or second output 124. In some embodiments, confidence scores 148 may be stored in a database 136 and retrieved by processor 106. In some embodiments, user may manually input confidence score 148. In some embodiments, processor 106 may determine confidence score 148 using a fuzzy set inference system as described in detail with respect to FIG. 14.

With continued reference to FIG. 1, in a non-limiting example, suppose processor 106 generates two distinct transformations A( ) and B( ) of N distinct original ECG recordings o1, o2, . . . o_N (first form data 116 and second form data 118 respectively); for instance, A(o1) may be a digital vector pdf obtained by asking first measurement device 142*a* to give a 40 Hz filtered version of o1 and B(o1) may be a digital vector obtained by asking a second measurement device 142*b* to create a 40 Hz filtered version of o1. Continuing the non-limiting example, processor 106 may generate a paired output 146: N pairs of digital vector pdfs (A(o1),B(o1)),(A(o2),B(o2)), . . . , (A(o_N),B(o_N)) and A(o1) may be compared to B(o1) and A(o_N) may be compared to B(o_N). In a non-limiting example, processor 106 may generate confidence score 148 that is represented by so, where s( ) is a value between 0 and 1 with an accuracy threshold 137 of t_S or ts has a specific sensitivity (Sen, t_S) and specificity (Spec, t_S). The processor 106 may generate confidence score 148 on the A( ), B( ) pairs: for instance, [s(A(o1)), s(B(o1))], [s(A(o2)), s(B(o2))], . . . [s(A(o_N)), s(B(o_N))]. Processor 106 may then determine under what circumstances the pairs has nearly the same sensitivity(Sen, t_S) and same specificity(Spec, t_S) on digital vector pdfs A or B. Continuing the non-limiting example, suppose ground truth data (e.g., first output XX and/or second output 124) is unknown and ground truth data representing $y_1$, $y_2$, model accuracy (sensitivity 128 and/or specificity 130), $y_N$ on each $o_i$, while each $y_i \in$ {False, True}indicating whether or not $o_i$ has the outcome of interest. Validated machine-learning model 102 and/or SaMD 126 may take in transformed ECGs (first form data 116 and/or second form data 118) and outputs scores (confidence score 148) from 0 to 1 according to a fixed function s. Denote by $a_i \in$ {Neg, Pos}, the classification output (confidence score 148) of validated machine-learning model 102 and/or SaMD 126 on $o_i$ with transformation A for first form data 116. That is, $$\text{if } s(A(o_i)) >= t_s : a_i = Pos$$
$$\text{if } s(A(o_i)) < t_s : a_i = Neg.$$

Continuing the non-limiting example, sensitivity_A may be sensitivity 128 of validated machine-learning model 102 and/or SaMD 126 for each first form data 116 of data pair 144, and specificity_A may be specificity 130 of validated machine-learning model 102 and/or SaMD 126 for each first form data 116 of data pair 144:

$$\text{sensitivity\_A} = \#\{i : a_i = Pos \text{ AND } y_i = \text{True}\}/\#\{i : y_i = \text{True}\}$$
$$\text{specificity\_A} = \#\{i : a_i = Neg \text{ AND } y_i = \text{False}\}/\#\{i : y_i = \text{False}.$$

Continuing the non-limiting example, sensitivity_B may be sensitivity 128 of validated machine-learning model 102 and/or SaMD 126 for each second form data 118 of data pair 144 for transformation B, and specificity_B may be specificity 130 of validated machine-learning model 102 and/or SaMD 126 for each second form data 118 of data pair 144 for transformation B:

$$\text{if } s(B(o_i)) >= t_s : b_i = Pos$$
$$\text{if } s(B(o_i)) < t_s : b_i = Neg$$

And, $$\text{sensitivity\_B} = \#\{i : b_i = Pos \text{ AND } y_i = \text{True}\}/\#\{i : y_i = \text{True}\}$$
$$\text{specificity\_B} = \#\{i : b_i = Neg \text{ AND } y_i = \text{False}\}/\#\{i : y_i = \text{False}\}$$

Also, prevalence p may be:

$$\text{prevalence } p = \#\{i : y_i = \text{True}\}/N.$$

Continuing the non-limiting example, assuming that transformation A that has been tested is known to be "good" (e.g., in terms of sensitivity 128 and specificity 130) on the distribution of ECGs that dataset O is coming from, closeness of s(B(o_i)) of transformation B to s(A(o_i)) may be determined. In some embodiments, the closeness of s(B (o_i)) to s(A(o_i)) may be quantified by:

$$m_{Apos \rightarrow Bneg} = \#\{i : a_i = Pos \text{ AND } b_i = Neg\}$$
$$m_{Aneg \rightarrow Bpos} = \#\{i : a_i = Neg \text{ AND } b_i = Pos\}.$$

The closeness of s(B(o_i)) to s(A(o_i)) may be utilized as lower-bound sensitivity_B in terms of sensitivity_A by:

$$\text{sensitivity}_B =$$

$$\frac{\#\{i : b_i = POS \text{ AND } y_i = \text{True}\}}{\#\{i : y_i = \text{True}\}} \geq \frac{\#\{i : a_i = Pos \text{ AND } b_i = Pos \text{ AND } y_i = \text{True}\}}{\#\{i : y_i = \text{True}\}} =$$

$$\frac{\#\{i : a_i = POS \text{ AND } y_i = \text{True}\} - \#\{i : a_i = Pos \text{ AND } b_i = Neg \text{ AND } y_i = \text{True}\}}{\#\{i : y_i = \text{True}\}} \geq$$

$$\frac{\#\{i : a_i = Pos \text{ AND } y_i = \text{True}\} - \#\{i : a_i = Pos \text{ AND } b_i = Neg\}}{\#\{i : y_i = \text{True}\}} =$$

-continued $$\text{sensitivity}_A - \frac{m_{Apos \to Bneg}}{\#\{i : y_i = True\}} = \text{sensitivity}_A - \frac{m_{Apos \to Bneg}}{Np}$$

Alternately, this can be written as:

$$\text{sensitivity}_A - \frac{m_{Apos \to Bneg}/\#\{i : a_i = Pos\}}{\#\{i : y_i = True\}/\#\{i : a_i = Pos\}} = \text{sensitivity}_A - \frac{r_{Apos \to Bneg}}{PPV}$$

Similarly, for specificity 130:

$$\text{specificity}_B =$$

$$\frac{\#\{i : b_i = Neg \ \text{AND} \ y_i = False\}}{\#\{i : y_i = False\}} \ge \frac{\#\{i : a_i = Neg \ \text{AND} \ b_i = Neg \ \text{AND} \ y_i = False\}}{\#\{i : y_i = False\}} =$$

$$\frac{\#\{i : a_i = Neg \ \text{AND} \ y_i = False\} - \#\{i : a_i = Neg \ \text{AND} \ b_i = Pos \ \text{AND} \ y_i = False}{\#\{i : y_i = False\}} \ge$$

$$\frac{\#\{i : a_i = Neg \ \text{AND} \ y_i = False\} - \#\{i : a_i = Neg \ \text{AND} \ b_i = Pos\}}{\#\{i : y_i = False\}} =$$

$$\text{specificity}_A - \frac{m_{Aneg \to Bpos}}{\#\{i : y_i = False\}} = \text{specificity}_A - \frac{m_{Aneg \to Bpos}}{N(1 - p)}$$

Alternately, this can be written as:

$$\text{specificity}_A - \frac{m_{Aneg \to Bpos}/\#\{i : a_i = Neg\}}{\#\{i : y_i = False\}/\#\{i : a_i = Neg\}} = \text{specificity}_A - \frac{r_{Aneg \to Bpos}}{NPV}$$

Continuing the non-limiting example, in the context of the following scenario:

N=1000

$5\% <= p <= 15\%$ sensitvity_A>=80% specificity_A>=80%

$m_{Apos \to Bneg}$=5

$m_{Aneg \to Bpos}$=20

Then the bounds may be sensitivity_B>=sensitivity_A−5/(1000*0.05)=0.8−0.1=0.7                    And specificity_B>=specificity_A−20/(1000*0.85)=0.8−0.024=0.78.

In some embodiments, by increasing the threshold (accuracy threshold 137) for B, better bounds on sensitivity_B may be obtained while keeping good bounds on specificity_B.

In some other embodiments, there might be other bounds for sensitivity 128 that can be tighter: for example, and without limitation, it can be shown that if the following condition holds (using the lower bound for sensitivity_B derived from sensitivity_A):

$$\frac{\text{specificity}_B}{1 - \text{specificity}_B} \ge \frac{\#\{i : b_i = Pos\}}{\#\{i : b_i = Neg\}}.$$

Then, $$\text{specificity}_B \ge \frac{\#\{i : b_i = Neg\} - (1 - \text{specificity}_B)Np}{N - Np},$$

where p may be bounded.

Additionally, continuing the non-limiting example, rather than assuming that every single Apos→Bneg switch is an actual error, processor 106 may model the likelihood that particular ECG is ground-truth "True" based on the A-score s(A(o_i)). That is, on a separate dataset coming from the same distribution as O came from, processor 106 may have estimates for Pr[y=True score=s] for each s from 0 to 1. In a non-limiting example, processor 106 may receive a dataset Q=$q_1$, $q_2$, model accuracy (sensitivity 128 and/or specificity 130), $q_M$, a dataset, where processor 106 have A-transformed scores (e.g., first form accuracy metric 132) and ground-truth (e.g., first output 122 and/or second output 124) but not B-transformed scores (second form accuracy metric 134). Processor 106 may then split "Positives" into "BorderlinePos" and "StrongPos" by the A-transformed score, and "Negatives" into "BorderlineNeg" and "Strong-Neg." In some embodiments, when BorderlinePos cases switch over to Neg and/or when BorderlineNeg cases switch over to Pos, they may not all be wrong. Suppose the score threshold (accuracy threshold 137) used originally is t. Borderline score thresholds may be set as $t_p$ and $t_n$ as following:

$t_p$=the 25 percentile score among the Pos scores in Q $t_n$=the 75 percentile score among the Neg scores in Q. 25% of Pos cases in Q may be BorderlinePos, and 25% of Neg cases in Q may be BorderlineNeg.

Continuing the non-limiting example, processor 106 may generate confidence score 148 using a forward Bayesian approach by estimating performance of B-transformed scores (e.g., second form accuracy metric 134) on the A/B paired dataset (paired data set 138). Continuing the non-limiting example, assuming that processor 106 have a dataset Q where A-transformed scores and ground-truth is known and dataset O where A-transformed scores and B-transformed scores is known. Additionally, assuming O and Q are coming from the same distribution, sensitivity_B (e.g., sample from a posterior distribution of sensitiviy_B) may be generated given all the information of Q and O. Exemplary codes for the Bayesian approach is provided below.

Continuing the non-limiting example, processor 106 may use a simple Bayesian approach. Additionally, code for this approach with simulated data is described below. Processor 106 may model P[y=1|s_A] as piece-wise constant on StrongNeg, BorderlineNeg, BorderlinePos and StrongPos ranges for s_A. Suppose a score threshold used originally is t and set the borderline score thresholds $t_p$ and $t_n$ say as follows:

$t_p$=the 25 percentile score among the Pos scores in Q $t_n$=the 75 percentile score among the Neg scores in Q. Then, $$StrongNeg : s\_A < t_n$$

$$BorderlineNeg : t_n < s\_A < t$$

$$BorderlinePos : t < s\_A < t_p$$

$$StrongPos : t_p < s\_A.$$

Then, in Bayesian fashion, processor 106 may estimate posteriors based on Q for the 4 parameters:

$$p_{StrongNeg} = P[y = 1 \mid s\_A \text{ is } StrongNeg]$$

$$p_{BorderlineNeg} = P[y = 1 \mid s\_A \text{ is } BorderlineNeg]$$

$$p_{BorderlinePos} = P[y = 1 \mid s\_A \text{ is } BorderlinePos]$$

$$p_{StrongPos} = P[y = 1 \mid s\_A \text{ is } StrongPos].$$

In a non-limiting example, it may be assumed that a non-informative Jeffreys Beta(0.5, 0.5) prior on each; the posteriors are Beta distributions based on observed counts.

Processor 106 may estimate sensitivity 128 of B-transformed scores using dataset O. Beta(0.5, 0.5) may be placed prior on sensitivity$_B$ and specificity$_B$. Processor 106 may model the posterior as follows:

$p(\text{sensitivity\_B} \mid s\_A_1, s\_A_2,$ model accuracy (sensitivity 128 and/or specificity 130), $s\_A_N$) =

$$\sum_{y_1, y_2, \ldots, y_N} p(\text{sensitivity}_B \mid y_1, y_2, \ldots, y_N)$$

$$Pr[y_1, y_2, \ldots, y_N \mid sA_1, sA_2, \ldots, sA_N] \propto$$

$$\sum_{y_1, y_2, \ldots, y_N} p(\text{specificity}_B \mid y_1, y_2, \ldots, y_N) Pr[y_1 \mid sA_1]$$

$$Pr[y_2 \mid sA_2] \ldots Pr[y_N \mid sA_N].$$

For a specific $y_1$, $y_2$, model accuracy (sensitivity 128 and/or specificity 130), $y_N$, the posterior $p(\text{sensitivity}_B|y_1, y_2, \ldots, y_N)$ may be Beta(#{i: s_B>=t & $y_i$=1}+0.5, #{i: s_B<t & $y_i$=1}+0.5). A similar identity may hold for specificity$_B$, with the posterior Beta(#{i: s_B<t & $y_i$=0}+0.5, #{i: s_B>=t & $y_i$=0}+0.5).

Processor 106 may sample from the posterior sensitivity$_B$ using the following procedure to estimate a posterior on sensitvity$_B$:

1. Sample $p_{StrongNeg}$, $p_{BorderlineNeg}$, $p_{BorderlinePos}$, $p_{StrongPos}$ from their posteriors from dataset Q.
2. Sample $y_1$, $y_2$, model accuracy (sensitivity 128 and/or specificity 130), $y_N$ according to the probabilities from Step 1.
3. Sample sensitvity$_B$ from the posterior Beta distribution described above.
4. Repeat 1-3 until processor 106 have a large number of samples of the posterior sensitivity$_B$ (e.g., 10000 samples)

Processor 106 can then report an estimate of the full posterior distribution; in particular processor 106 may report estimated 95% credible interval for sensitivity$_B$ along with posterior mean. A similar procedure may be done on specificity$_B$.

Continuing the non-limiting example, processor 106 may estimate the posterior distribution for P[y=1|s_A] as a function of s_A ranging from 0 to 1 from dataset Q. To allow for substantial modeling flexibility, processor 106 may model logit(P[y=1|s_A]) as a linear spline on logit(s_A) with knots at (i) quartiles of the logit(s_A) distribution where s_A<t, and (ii) quartiles of the logit(s_A) distribution where s_A>t. This is a total of 7 knots. Processor 106 may use logit(s_A) as the input space because s_A may be originally trained to approximate a logistic probability. Processor 106 may then simulate $y_1$, $y_2$, model accuracy (sensitivity 128 and/or specificity 130), $y_N$ in dataset O based on the estimate for P[y=1|s_A] from dataset Q. As a non-limiting example, processor 106 may sample the spline parameters from their posteriors to get a function P[y=1|s_A]. Then, since P[$y_1$, $y_2$, model accuracy (sensitivity 128 and/or specificity 130), $y_N$, $A_1$, $A_2$, model accuracy (sensitivity 128 and/or specificity 130), $A_N$] is proportional to P[$y_1$|$A_1$]P[$y_2$|$A_2$] model accuracy (sensitivity 128 and/or specificity 130) P[$y_N$|$A_N$], processor 106 may then draw each $y_1$ from P[y=1|s_A=A], which is one point from the P[y=1|s_A] estimate. Then for each simulation $y_1$, $y_2$, model accuracy (sensitivity 128 and/or specificity 130), $y_N$, processor 106 may sample a sensitvity_B parameter by using the posterior distribution P[sensitivity_B|$y_1$, $y_2$, model accuracy (sensitivity 128 and/or specificity 130), $y_N$]. Processor 106 may assume a non-informative Jeffreys Beta(0.5, 0.5) for sensitivity_B. That is, for the posterior, Processor 106 may sample from Beta(#{i: s_B>=t & $y_i$=1}+0.5, #{i: s_B<t & $y_i$=1}+0.5). Processor 106 may repeat the steps many times and use the resulting sample as an estimate for the posterior distribution on sensitivity_B. Processor 106 may compute credible intervals by taking percentiles of the simulated samples from the posterior.

Continuing the non-limiting example, processor 106 may us a reverse Bayesian approach by estimating performance of B-transformed scores on an original holdout set Q with A-transformed scores and ground-truth. In a non-limiting example, assume that the prevalence, PPV, NPV, and the like are similar in a paired data set (e.g., data set O) as in the original validation set (e.g., data set Q) may not be realistic. Instead, processor 106 may use the dataset O to infer P(B|A) and estimate the sensitivity 128 and/or specificity 130 of B-transformed ECG scores on the original validation set Q. Additionally, continuing the non-limiting example, assume that the same relation between B-scores and A-score holds in both populations. Let the binary version of B be $B_{bin}$ defined as follows:

$$B_{bin} = 1 \text{ if score\_B} >= t = 0 \text{ otherwise.}$$

Define $t_n$, $t_p$ similarly as before except this time on dataset O rather than Q:

$t_p$=the 25 percentile score among the Pos scores in O $t_n$=the 75 percentile score among the Neg scores in O. Then, define the following classes for s_A:

$$StrongNeg : s\_A < t_n$$

$$BorderlineNeg : t_n < s\_A < t$$

-continued $$BorderlinePos: t < \text{s\_A} < t_p$$

$$StrongPos: t_p < \text{s\_A}.$$

Here, processor 106 may estimate posteriors based on O for the following 4 parameters:

$$p_{Bbin|AStrongNeg} = P[B_{bin} = 1 \mid \text{s\_A is } StrongNeg]$$

$$p_{Bbin|ABorderlineNeg} = P[B_{bin} = 1 \mid \text{s\_A is } BorderlineNeg]$$

$$p_{Bbin|ABorderlinePos} = P[B_{bin} = 1 \mid \text{s\_A is } BorderlinePos]$$

$$p_{Bbin|AStrongPos} = P[B_{bin} = 1 \mid \text{s\_A is } StrongPos].$$

Then, processor 106 may simulate $B_{bin}$ on dataset Q: once processor 106 may have the simulated $B_{bin}$, processor 106 may then have the sensitivity 128 and/or specificity 130 on dataset Q, and processor 106 may can use these simulations to get a full posterior for sensitivity$_B$ and specificity$_B$ on the Q population.

Processor 106 may model the posterior as follows:

$$p(\text{sensitivity\_B} \mid \text{s\_A}_1, \text{s\_A}_2,$$

$$\text{model accuracy (sensitivity 128 and/or specificity 130)}, \text{s\_A}_M) =$$

$$\sum\nolimits_{B_{bin1}, B_{bin2}, \dots, B_{binM}} p(\text{sensitivity}_B \mid B_{bin1}, B_{bin2}, \dots, B_{binM})$$

$$Pr[B_{bin1}, B_{bin2}, \dots, B_{binM} \mid sA_1, sA_2, \dots, sA_M] \propto$$

$$\sum_{B_{bin1}, B_{bin2}, \dots, B_{binM}} p(\text{sensitivity}_B \mid B_{bin1}, B_{bin2}, \dots, B_{binM})$$

$$Pr([B_{bin1} \mid sA_1]Pr[B_{bin2} \mid sA_2] \dots Pr[B_{binM} \mid sA_M] \text{ For a specific } B_{bin1},$$

$$B_{bin2}, \dots, B_{binM}, \text{ the posterior } p(\text{sensitivity}_B \mid B_{bin1}, B_{bin2}, \dots, B_{binM})$$

$$\text{is Beta}(\#\{j: B_{binj} = 1 \ \& \ y_j = 1\}0.5, \#\{j: B_{binj} = 1 \ \& \ y_j = 1\} + 0.5)$$

Here the $y_j$ may be the observed ground-truths in dataset Q.

Processor 106 may sample from this posterior sensitivity$_B$ using the following procedure:

1. Sample $p_{Bbin|AStrongNeg}$, $p_{Bbin|ABorderlineNeg}$, $p_{Bbin|ABorderlinePos}$, $p_{Bbin|AStrongPos}$ from their posteriors from dataset O.
2. Sample $B_{bin1}$, $B_{bin2}$, . . . , $B_{binM}$ according to the probabilities from Step 1.
3. Sample sensitvity$_B$ (on dataset Q) from the posterior Beta distribution described above.
4. Repeat 1-3 until processor 106 may have a large number of samples of the posterior sensitivity$_B$ (say 10,000 samples)

Processor 106 may then report the estimate of the full posterior distribution; in particular processor 106 may report estimated 95% credible interval for sensitivity$_B$ (on the dataset Q population) along with posterior mean. And these may be similar for specificity$_B$.

With continued reference to FIG. 1, in some embodiments, processor 106 may generate a user interface 150. In some embodiments, user interface 150 may be configured to display first form accuracy metric 132, first output 122, second output 124, paired output 146, first form data 116, second form data 118, first data form 120a, second form data 118, second form accuracy metric 134, whether second form accuracy metric 134 exceeds accuracy threshold 137, and the like on a remote device 152. For the purposes of this disclosure, a "remote device" is an external device to processor 106. As a non-limiting example, remote device 152 may include a laptop, desktop, tablet, mobile phone, smart phone, smart watch, kiosk, screen, smart headset, or things of the like. In some embodiments, remote device 152 may include an interface configured to receive inputs from a user. In some embodiments, user may manually input any data into apparatus 100 using remote device 152. In some embodiments, user may have a capability to process, store or transmit any information independently. For the purposes of this disclosure, a "user interface" is a means by which a user and a computer system interact; for example through the use of input devices and software. A user interface may include a graphical user interface (GUI), command line interface (CLI), menu-driven user interface, touch user interface, voice user interface (VUI), form-based user interface, any combination thereof and the like. In some embodiments, user interface may operate on and/or be communicatively connected to a decentralized platform, metaverse, and/or a decentralized exchange platform associated with the user. For example, a user may interact with user interface in virtual reality. In some embodiments, a user may interact with the use interface using a computing device distinct from and communicatively connected to at least a processor 106. For example, a smart phone, smart, tablet, or laptop operated by a user. In an embodiment, user interface may include a graphical user interface. A "graphical user interface," as used herein, is a graphical form of user interface that allows users to interact with electronic devices. In some embodiments, GUI may include icons, menus, other visual indicators or representations (graphics), audio indicators such as primary notation, and display information and related user controls. A menu may contain a list of choices and may allow users to select one from them. A menu bar may be displayed horizontally across the screen such as pull-down menu. When any option is clicked in this menu, then the pull-down menu may appear. A menu may include a context menu that appears only when the user performs a specific action. An example of this is pressing the right mouse button. When this is done, a menu may appear under the cursor. Files, programs, web pages and the like may be represented using a small picture in a graphical user interface. For example, links to decentralized platforms as described in this disclosure may be incorporated using icons. Using an icon may be a fast way to open documents, run programs etc. because clicking on them yields instant access.

Exemplary codes for a Bayesian approach is provided below.

```
import numpy as np
import scipy.stats
from scipy.special import logit, expit
from scipy.interpolate import interp1d
from sklearn.gaussian_process import GaussianProcess-
    Regressor, kernels
from statsmodels.stats.proportion import proportion_con-
    fint
import matplotlib.pyplot as plt
import seaborn as sns
from tqdm import tqdm
def compute_spline_y(x, knots, beta):
    """"given a linear spline characterized by knots at knots
        and parameters
    beta (intercept+slope+slope deltas), compute the spline
        values at x"""
```

```
    assert len(beta)==len(knots)+2
    y=beta[0]+beta[l]*x
    for i in range(len(knots)):
        y+=beta[i+2]*np.maximum(0, x-knots[i])
    return y
def compute_prev_sens_spec(y, A, t):
    """compute prevalence, sensitivity, and specificity
        given ground-truth y, test values A, and threshold
        t"""
    prev=np.mean(y)
    sens=np.mean((A>=t) & (y==1))/prev
    spec=np.mean((A<t) & (y==0))/(1-prev)
    return prev, sens, spec
def sim_A_y(M, knots, beta):
    A=scipy.stats.beta.rvs(0.1, 2.4, size=M)
    logit_A=np.clip(logit(A), -10, 10)
    A=expit(logit_A)
    logit_p_y_given_A_sim=compute_spline_y(logit_A,
        knots, beta)
    p_y_given_A_sim=expit(logit_p_y_given_A_sim)
    y_given_A_sim=(np.random.rand(M)<p_y_give-
        n_A_sim).astype(int)
    return A, y_given_A_sim
def            get_logit_B_from_logit_A_fn(logit_A,
    noise_sigma=1):
    """perturb logit_A to get simulated logit_B"""
    gp=GaussianProcessRegressor(
        kernel=kernels.ConstantKernel(noise_sigma,
            constant_value_bounds="fixed")
        *kernels.RBF(1.0, length_scale_bounds="fixed")
        +kernels.WhiteKernel(noise_level=noise_sigma/4,
            noise_level_bounds="fixed"),
    )
    logit_A_grid=np.linspace(logit_A.mino,      logit_A-
        .maxo, 1000)
    simple_gp_noise_vals_grid=gp.sample_y(logit_A_gri-
        d.reshape(-1, 1), 1).flatten( )
    noise_interp_fn=interpld(logit_A_grid,       simple_
        gp_noise_vals_grid, kind="linear")
    return lambda x: x+noise_interp_fn(x)
def get_ppv_posteriors_strong_borderline(A, y, t):
    t_n=np.quantile(A[A<t], 0.75)
    t_p=np.quantile(A[A>=t], 0.25)
    strong_neg_posterior=scipy.stats.beta(
        ((y==1)   &   (A<t_n)).sum(   ),   ((y==0)   &
            (A<t_n)).sum( )
    )
    borderline_neg_posterior=scipy.stats.beta(
        ((y==1) & (A>=t_n) & (A<t)).sum( ),
        ((y==0) & (A>=t_n) & (A<t)).sum( ),
    )
    borderline_pos_posterior=scipy.stats.beta(
        ((y==1) & (A>=t) & (A<t_p)).sum( ),
        ((y==0) & (A>=t) & (A<t_p)).sum( ),
    )
    strong_pos_posterior=scipy.stats.beta(
        ((y==1) & (A>=t_p)).sum( ), ((y==0) & (A>=t_p))
            .sum( )
    )
    thresholds=(t_n, t, t_p)
    posteriors=(
        strong_neg_posterior,
        borderline_neg_posterior,
        borderline_pos_posterior,
        strong_pos_posterior,
```

```
    )
    return thresholds, posteriors
def sim_y_from_strong_borderline_posteriors(
    A, t_n, t, t_p, posteriors, n_samples=10000
);
    (
        strong_neg_posterior,
        borderline_neg_posterior,
        borderline_pos_posterior,
        strong_pos_posterior,
    )=posteriors
    i_strong_neg=A<t_n
    i_borderline_neg=(A>=t_n) & (A<t)
    i_borderline_pos=(A>=t) & (A<t_p)
    i_strong_pos=A>=t_p
    p_strong_negs=strong_neg_posterior.rvs(n_samples)
    p_borderline_negs=borderline_neg_posterior.rvs
        (n_samples)
    p_borderline_poss=borderline_pos_posterior.rvs
        (n_samples)
    p_strong_poss=strong_pos_posterior.rvs(n_samples)
    y_sims=np.zeros((n_samples, A.shape[0]))
    for i_sample in tqdm(range(n_samples)):
        y_sim=np.zeros(A.shape[0])
        y_sim[i_strong_neg](
            np.random.rand(i_strong_neg.sum(           ))
                <p_strong_negs[i_sample]
        )
        y_sim[i_borderline_neg](
            np.random.rand(i_borderline_neg.sum(  ))<p_bor-
                derline_negs[i_sample]
        )
        y_sim[i_borderline_pos](
            np.random.rand(i_borderline_pos.sum(  ))<p_bor-
                derline_poss[i_sample]
        )
        y_sim[i_strong_pos](
            np.random.rand(i_strong_pos.sum(         ))<p_
                strong_poss[i_sample]
        )
        y_sims[i_sample]=y_sim
    return y_sims
def sim_sens_B(y, B, t):
    sens_B_posterior=scipy.stats.beta(
        0.5+((y==1) & (B>=t)).sum( ),
        0.5+((y==1) & (B<t)).sum( ),
    )
    return sens_B_posterior.rvs( )
def sim_spec_B(y, B, t):
    spec_B_posterior=scipy.stats.beta(
        0.5+((y==0) & (B<t)).sum( ),
        0.5+((y==0) & (B>=t)).sum( ),
    )
    return spec_B_posterior.rvs( )
def sample_sens_B_spec_B_posteriors(A, B, t_n, t, t_p,
    Q_posteriors, n_samples=10000):
    y_sims=sim_y_from_strong_borderline_posteriors(
        A, t_n, t, t_p, Q_posteriors, n_samples=n_samples
    )
    sens_B_samples=[sim_sens_B(y, B, t) for y in y_sims]
    y_sims=sim_y_from_strong_borderline_posteriors(
        A, t_n, t, t_p, Q_posteriors, n_samples=n_samples
    )
    spec_B_samples=[sim_spec_B(y, B, t) for y in y_sims]
    return sens_B_samples, spec_B_samples
def counting_bound_sens_diff(A, B, t, min_prev):
    assert A.shape==B.shape
```

```
n_apos_bneg=((A>=t) & (B<t)).sum( )
return n_apos_bneg/(A.shape[0]*min_prev)
M=20000
knots=np.array([−6, −4, −2, 0, 3, 5, 7])
beta=np.array([−2, 0.5, 0.2, 0.1, 0.2, 0, 0, −0.4, −0.1])
assert len(beta)==len(knots)+2
t=0.06
A, y=sim_A_y(M, knots, beta)
sns.histplot(A)
plt.show( )
print("(prev_A_Q,    sens_A_Q,    spec_A_Q):",   com-
    pute_prev_sens_spec(y, A, t))
sens_A_CI=proportion_confint(
    ((y==1) & (A>=t)).sum( ), (y==1).sum( ), alpha=0.05,
        method="wilson"
)
print("sens_A_Q 95% *Conf*interval:", sens_A_CI)
sens_A_CI_1=sens_A_CI[0]
prev_ci=proportion_confint(y.sum( ),  M,  alpha=0.05,
    method="wilson")
print("prev 95% *Conf*interval:", prev_ci)
prev_ci_1=prev_ci[0]
(t_n,                     t,                     t_p),
    Q_posteriors=get_ppv_posteriors_strong_borderline
    (A, y, t)
#B_noise_sigma=0.05
B_noise_sigma=0.2
Nbig=10000000
Abig, ybig=sim_A_y(Nbig, knots, beta)
logit_A_to_logit_B_fn=get_logit_B_from_logit_A_fn(
    logit(Abig), noise_sigma=B_noise_sigma
)
Bbig=expit(logit_A_to_logit_B_fn(logit(Abig)))
plt.scatter(Abig, Bbig)
plt.show( )
print("(prev_A,    sens_A,    spec_A):",    compute_pre-
    v_sens_spec(ybig, Abig, t))
print("(prev_B,    sens_B,    spec_B):",    compute_pre-
    v_sens_spec(ybig, Bbig, t))
N=5000
A_O, y_O=sim_A_y(N, knots, beta)
B_O=expit(logit_A_to_logit_B_fn(logit(A_O)))
sens_B_posteriors,
    spec_B_posteriors=sample_sens_B_spec_B_posteriors(
    A_O, B_O, t_n, t, t_p, Q_posteriors, n_samples=10000
)
print(
    "sens_B posterior mean (95% credible interval):",
    np.mean(sens_B_posteriors),
    np.quantile(sens_B_posteriors, [0.025, 0.975]),
)
print(
    "spec_B posterior mean (95% credible interval):",
    np.mean(spec_B_posteriors),
    np.quantile(spec_B_posteriors, [0.025, 0.975]),
)
print(
    "counting bound sens_B min:",
    sens_A_CI_1−counting_bound_sens_diff(A_O,  B_O,
        t, prev_ci_1),
)
```

Figure 2:
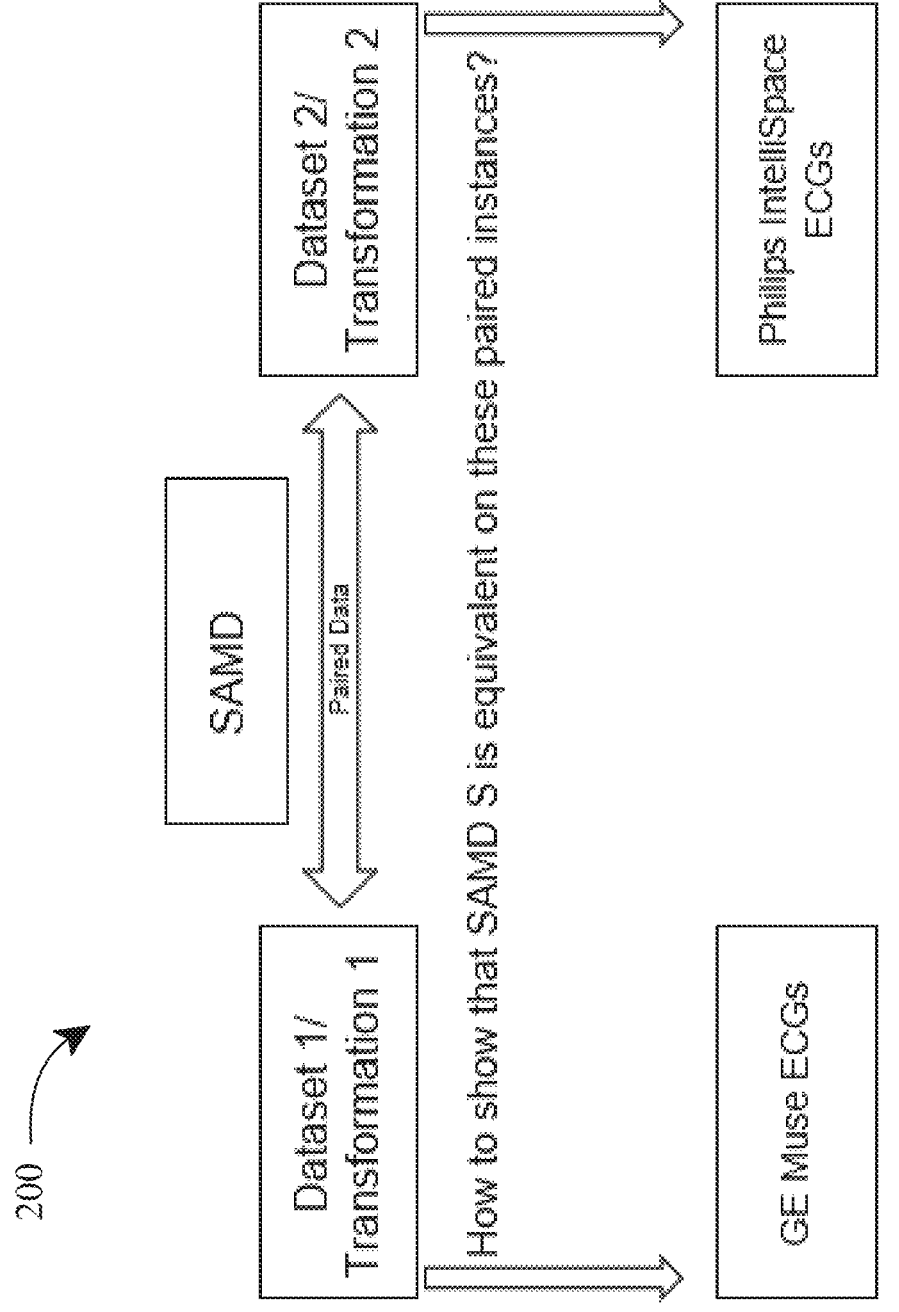
FIG. 2 illustrates an exemplary scenario of using a validated machine-learning model.

Referring now to FIG. 2, a block diagram of an exemplary scenario 200 of using a validated machine-learning model 102. In some embodiments, processor 106 may receive dataset 1 or transformation 1 (e.g., first form data 116) and dataset 2 or transformation 2 (e.g., second form data 118) from GE Muse ECGs® (first measurement device 142a) and Philips IntelliSpace ECGs® (second measurement device 142b). These datasets may be used for SaMD 126 (validated machine-learning model 102) and may be compared as a paired data (data pair 144 or paired output 146). By comparing the paired data, processor 106 may get estimates of sensitivity 128 and/or specificity 130 for Philips IntelliSpace ECGs® when ground-truth (GT) information is unavailable. Scenario 200 may represent a ground step or method for deriving equivalence by leveraging paired data and previously validated performance metrics from one transformation (e.g., GE Muse ECGs®) to infer performance for the other transformation (e.g., Philips ECGs®).

Figure 3:
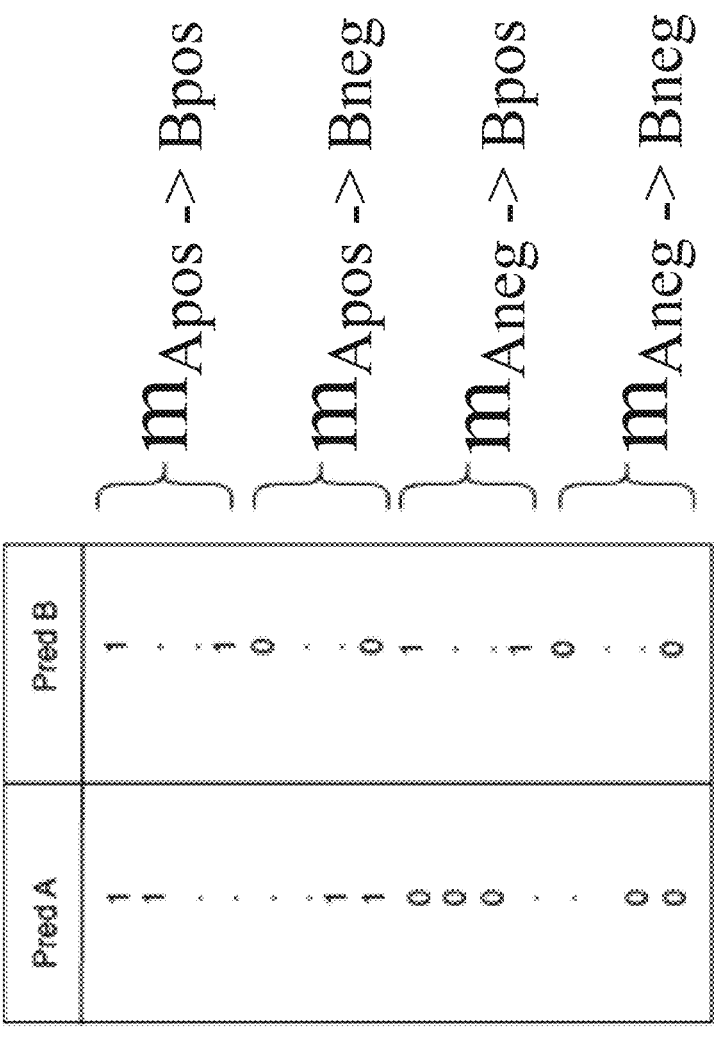
FIG. 3 illustrates an exemplary table for bounding sensitivity and specificity across paired data.

Referring now to FIG. 3, an exemplary table 300 for bounding sensitivity 128 and specificity 130 across paired data is illustrated. In FIG. 3. In some embodiments, paired data in table 300 includes scores from both transformations (first form data 116 and second form data 118). Transformation A (first form data 116) may include full information and the original test set (e.g., validated training set 110) with GT and clinical validation set. Transformation B (second form data 118) that needs to be analyzed for second form accuracy metric 134. The paired data may be utilized to estimate the performance metrics (second form accuracy metric 134) of a second transformation (second form data 118). Sensitivity 128 and specificity 130 may be initially calculated based on an assumption that every classification flip between transformations represents an error. For instance, in a scenario with N=1000, p (prevalence) between 5% and 15%, $m_{Apos} \rightarrow B_{neg}$=5, $m_{Aneg} \rightarrow B_{pos}$=20 and a baseline sensitivity 128 ($Sen_A$) and specificity 130 ($spec_A$) of 80% for the first transformation, the estimated bounds for the second transformation may be approximately 70% sensitivity 128 and 78% specificity 130. In a non-limiting example, N=1000; so with p=5%, 50 GT pos, with 80% sen, at least 40 pred pos; 5 flips imply at least 35 pred +ve in B, so 35/50 implying 70% Sen. These may be implemented as reference to FIGS. 1-2. This can be derived using the following:

$$Sen_B \geq Sen_A - \frac{m_{Apos->Bneg}}{N \cdot p}$$

$$Spec_B \geq Spec_A - \frac{m_{Aneg->Bpos}}{N \cdot (1-p)}$$

Figure 4:
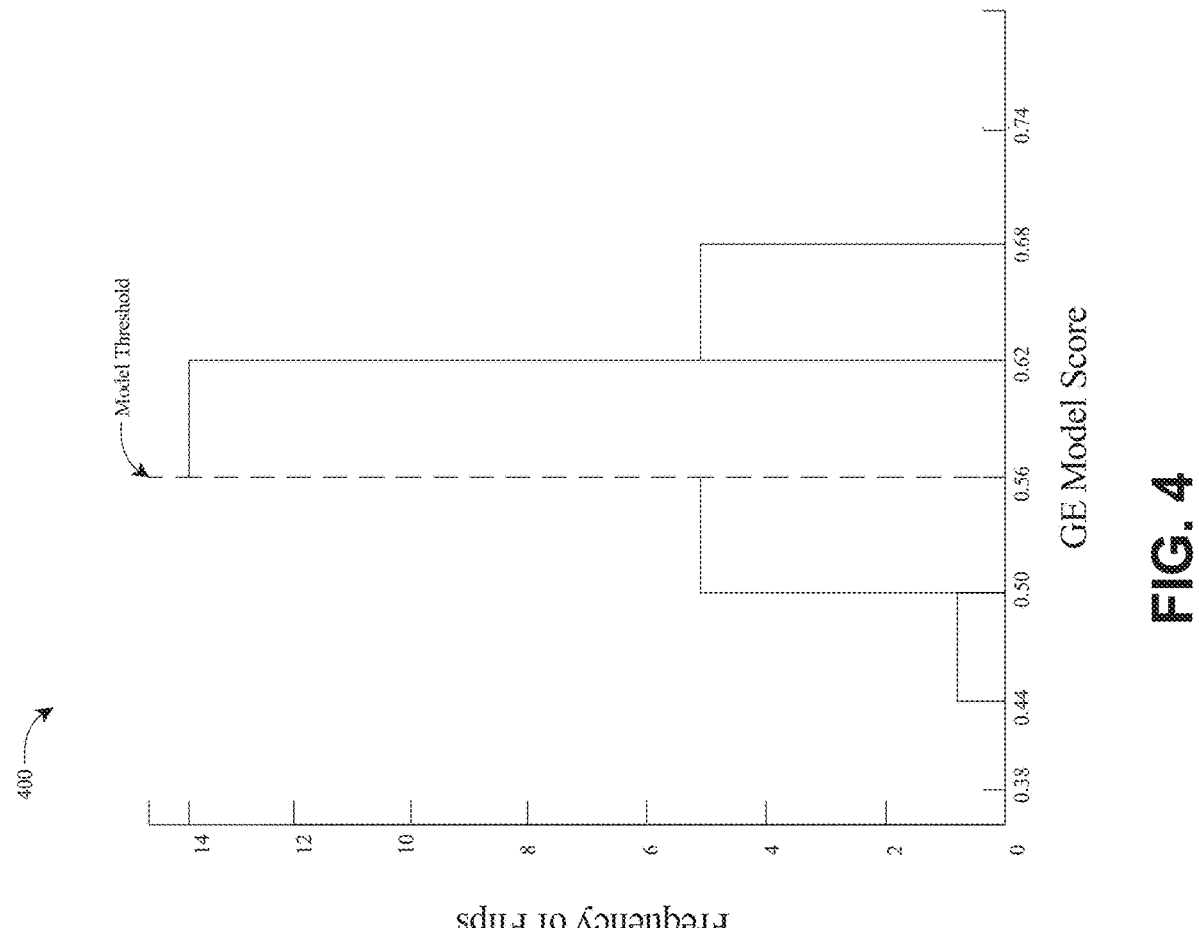
FIG. 4 illustrates an exemplary graph that shows classification flips are predominantly concentrated in the near-threshold region.

Referring now to FIG. 4, an exemplary graph 400 that shows classification flips are predominantly concentrated in the near-threshold region (model threshold) is illustrated. The graph 400 is created by comparing datasets from GE Muse ECGs® and Philips IntelliSpace ECGs®. In some embodiments, bounds used in FIGS. 2 and 3 may be considered very loose because every flip made is assumed to be an erroneous one. These may be implemented as reference to FIGS. 1-3.

Figure 5:
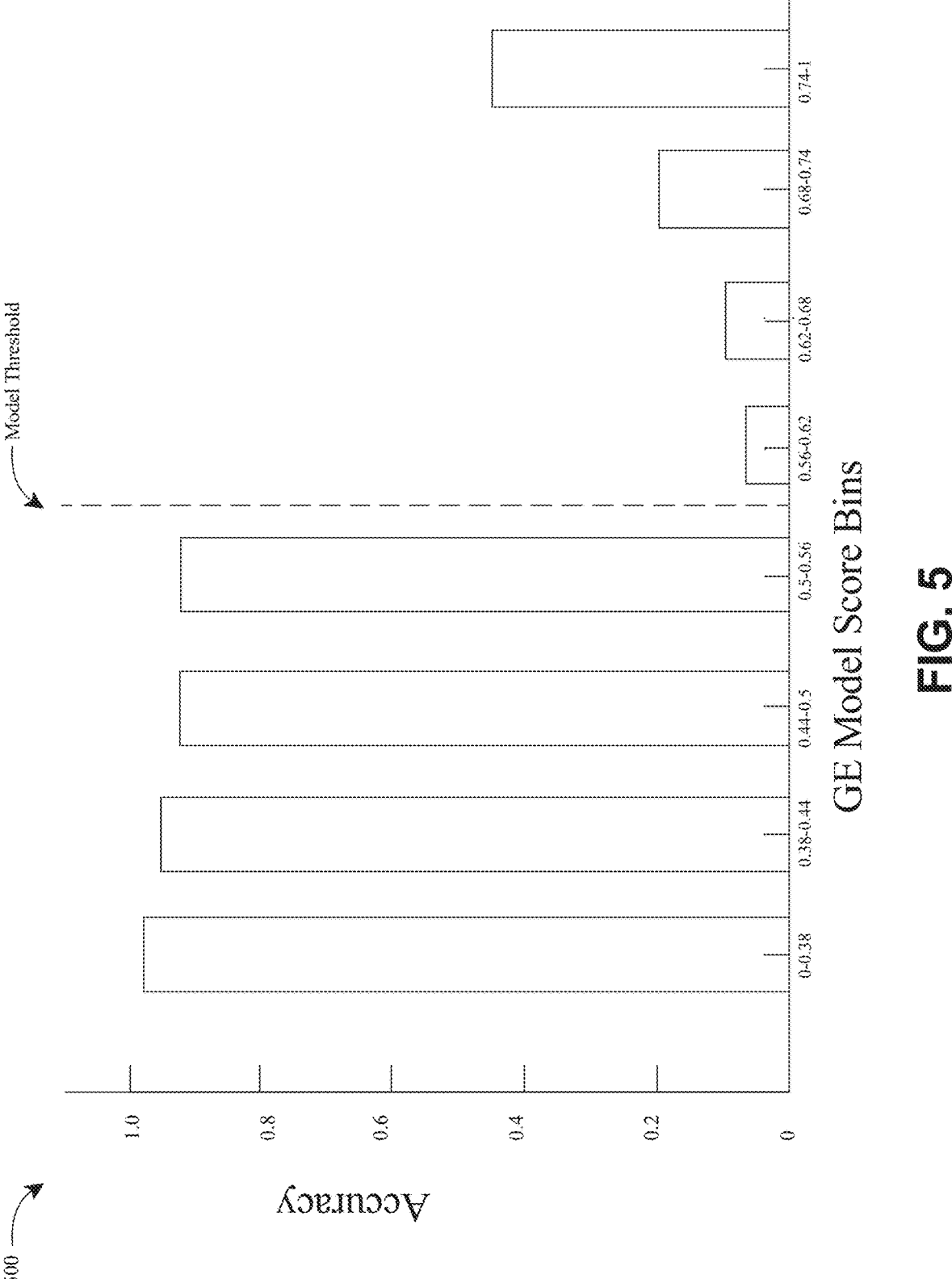
FIG. 5 illustrates an exemplary graph that shows degrade of a performance of software as a medical device (SaMD) compared to overall performance in the near-threshold region.

Referring now to FIG. 5, an exemplary graph 500 that shows degrade of a performance of SaMD compared to overall performance in the near-threshold region (model threshold) is illustrated. The graph 500 shows left ventricular ejection fraction (LVEF) model accuracy on clinical validation set wrt model score. In some embodiments, bounds used in FIGS. 2 and 3 may be considered very loose because every flip made is assumed to be an erroneous one. These may be implemented as reference to FIGS. 1-4.

Figure 6:
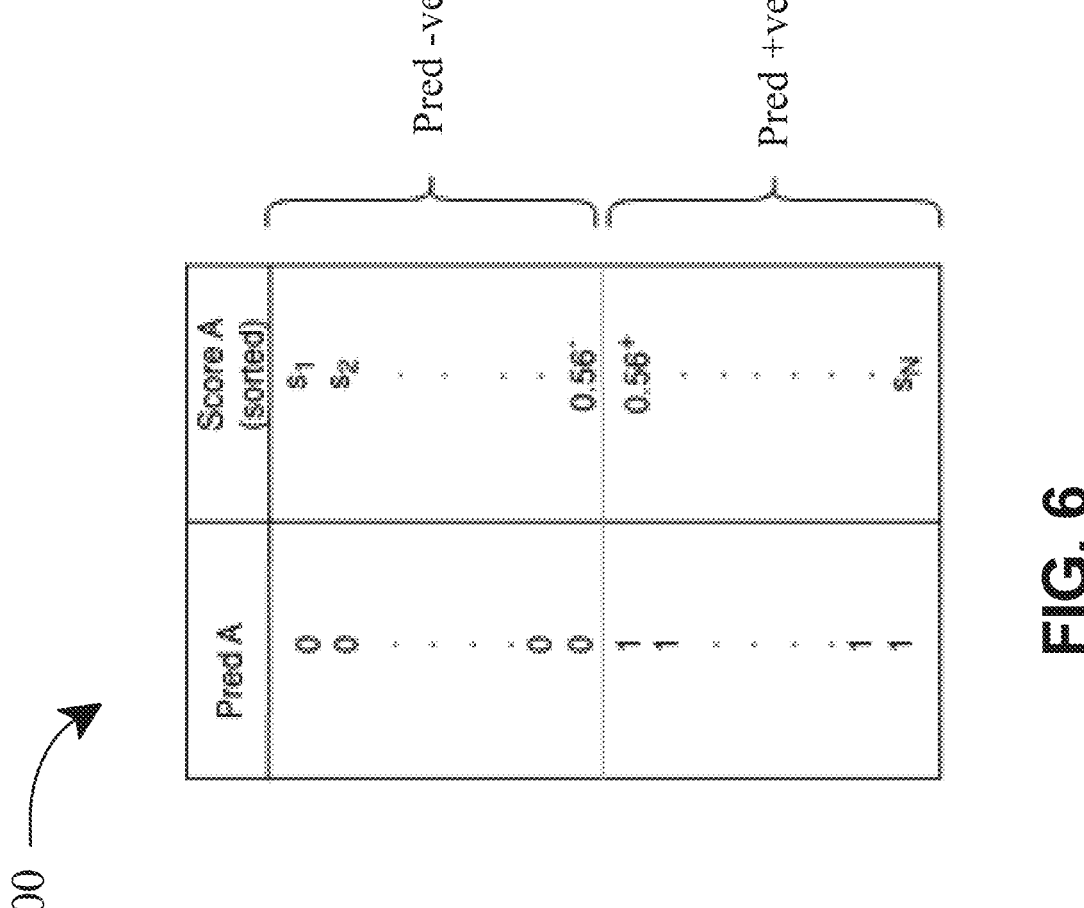
FIG. 6 illustrates an exemplary table of scored paired data.

Referring now to FIG. 6, an exemplary table 600 of scored paired data is illustrated. In some embodiments, binary predictions may be simulated on a validation set and get estimates for metrics, where model scores are known but not GT for the paired data have and GT and transformation 1 scores are known but not metrics for transformation 2 for validation data. These may be implemented as reference to FIGS. 1-5. The bounds can get tighter as following:

$$p_{Bpin|AStrongNeg} = P[B_{bin} = 1 \mid s\_A \text{ is } StrongNeg]$$

$$p_{Bpin|ABorderlineNeg} = P[B_{bin} = 1 \mid s\_A \text{ is } BorderlineNeg]$$

$$p_{Bpin|ABorderlinePos} = P[B_{bin} = 1 \mid s\_A \text{ is } BorderlinePos]$$

$$p_{Bbin|AStrongPos} = P[B_{bin} = 1 \mid s\_A \text{ is } StrongPos].$$

Figure 7:
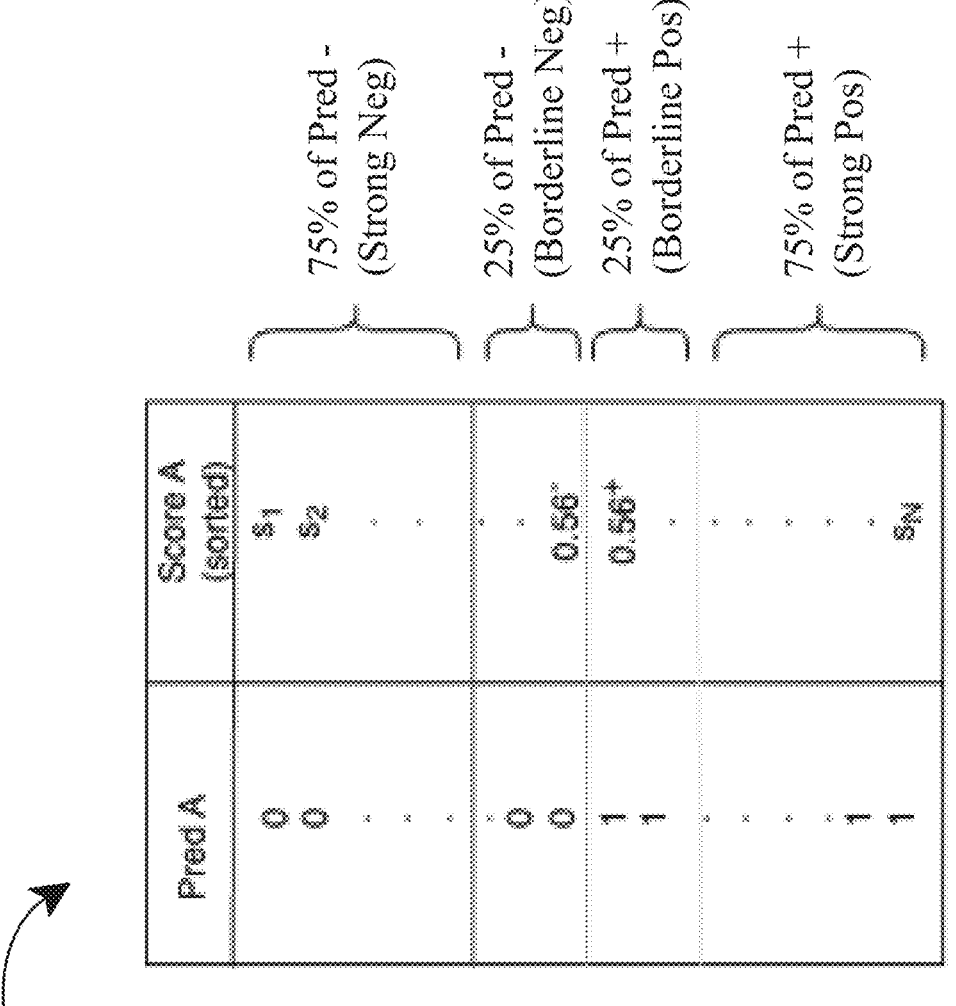
FIG. 7 illustrates an exemplary table of scored paired data with four types of scores.

Referring now to FIG. 7, an exemplary table 700 of scored paired data with four types of scores is illustrated. In some embodiments, binary predictions may be simulated on a validation set and get estimates for metrics, where model scores are known but not GT for the paired data have and GT and transformation 1 scores are known but not metrics for transformation 2 for validation data. These may be implemented as reference to FIGS. 1-6. The bounds can get tighter as following:

$$p_{Bbin|AStrongNeg} = P[B_{bin} = 1 \mid s\_A \text{ is } StrongNeg]$$

$$p_{Bpin|ABorderlineNeg} = P[B_{bin} = 1 \mid s\_A \text{ is } BorderlineNeg]$$

$$p_{Bbin|ABorderlinePos} = P[B_{bin} = 1 \mid s\_A \text{ is } BorderlinePos]$$

$$p_{Bbin|AStrongPos} = P[B_{bin} = 1 \mid s\_A \text{ is } StrongPos].$$

Figure 8:
FIG. 8 illustrates an exemplary table of paired data and validation data.

Referring now to FIG. 8, an exemplary table 800 of paired data and validation data is illustrated. In some embodiments, binary predictions may be simulated on a validation set and get estimates for metrics, where model scores are known but not GT for the paired data have and GT and transformation 1 scores are known but not metrics for transformation 2 for validation data. These may be implemented as reference to FIGS. 1-7. The bounds can get tighter as following:

$$p_{Bin|AStrongNeg} = P[B_{bin} = 1 \mid s\_A \text{ is } StrongNeg]$$

$$p_{Bbin|ABorderlineNeg} = P[B_{bin} = 1 \mid s\_A \text{ is } BorderlineNeg]$$

$$p_{Bbin|ABorderlinePos} = P[B_{bin} = 1 \mid s\_A \text{ is } BorderlinePos]$$

$$p_{Bbin|AAStrongPos} = P[B_{bin} = 1 \mid s\_A \text{ is } StrongPos].$$

Figure 9:
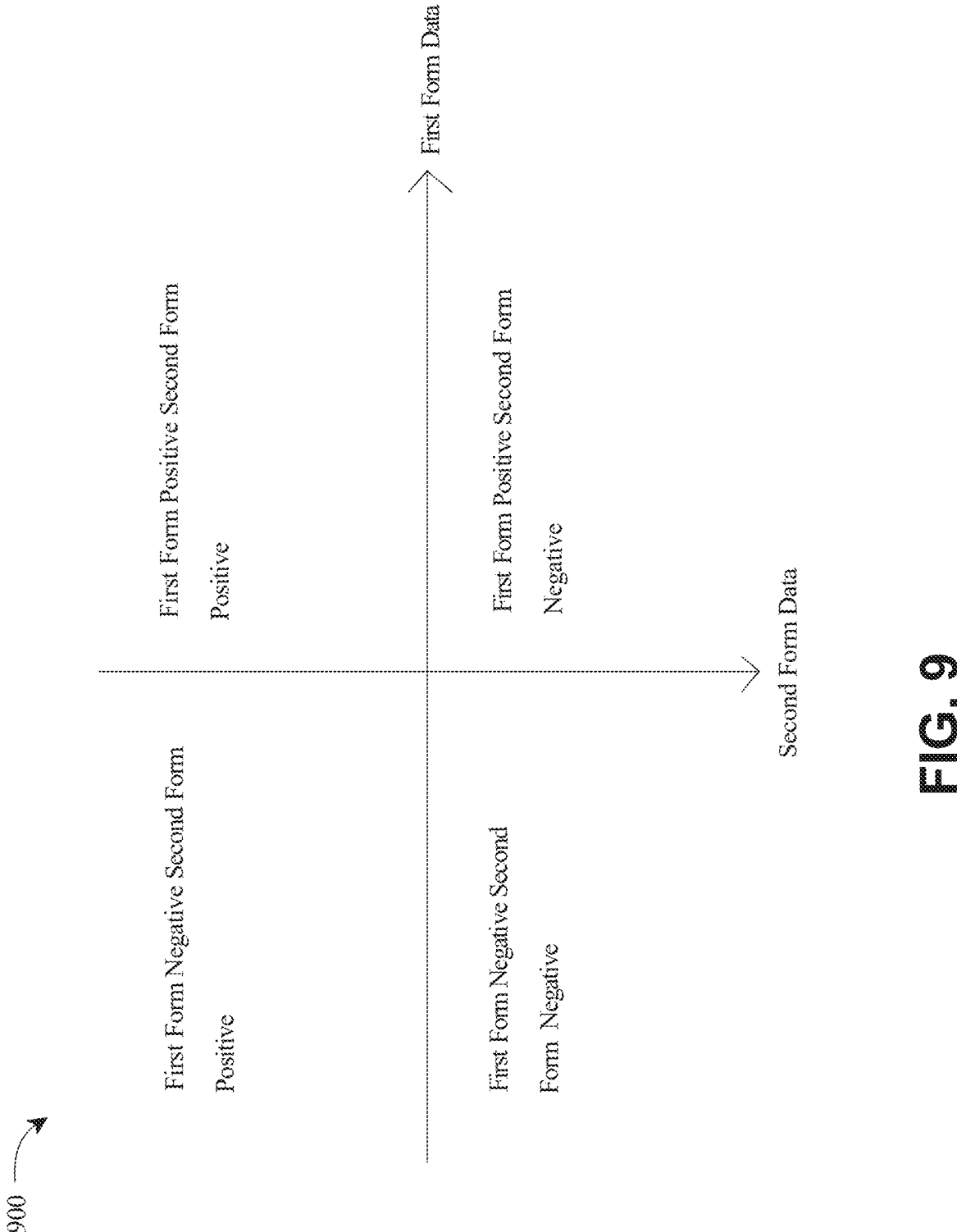
FIG. 9 illustrates an exemplary graph of distribution of confidence scores.

Referring now to FIG. 9, an exemplary graph 900 of distribution of confidence scores is illustrated. The graph 900 presents a two-dimensional representation where the axes correspond to first form data and second form data, with each axis divided into positive and negative classifications. The quadrants of the graph 900 represent the relationship between the classifications of first form data and second form data. The top-right quadrant represents instances where both first form data and second form data are classified as positive, while the bottom-left quadrant corresponds to cases where both are classified as negative. The top-left quadrant represents cases where the first form data is classified as negative and the second form data as positive. The bottom-right quadrant indicates the first form data classified as positive and the second form data as negative. The graph 900 can be used to calculate accuracy metric (second form accuracy metric 134) by analyzing the distribution of data points across these quadrants. These may be implemented as reference to FIGS. 1-8.

Referring now to FIG. 10, an exemplary user interface 1050 on a remote device 152 is illustrated. In some embodiments, user interface 1050 may display any information related to first form data 116 and second form data 118 on a remote device 152. In a non-limiting example, user interface 1050 may display a second form accuracy metric 134 (sensitivity 128 and specificity 130). These may be implemented as reference to FIGS. 1-9.

Figure 11:
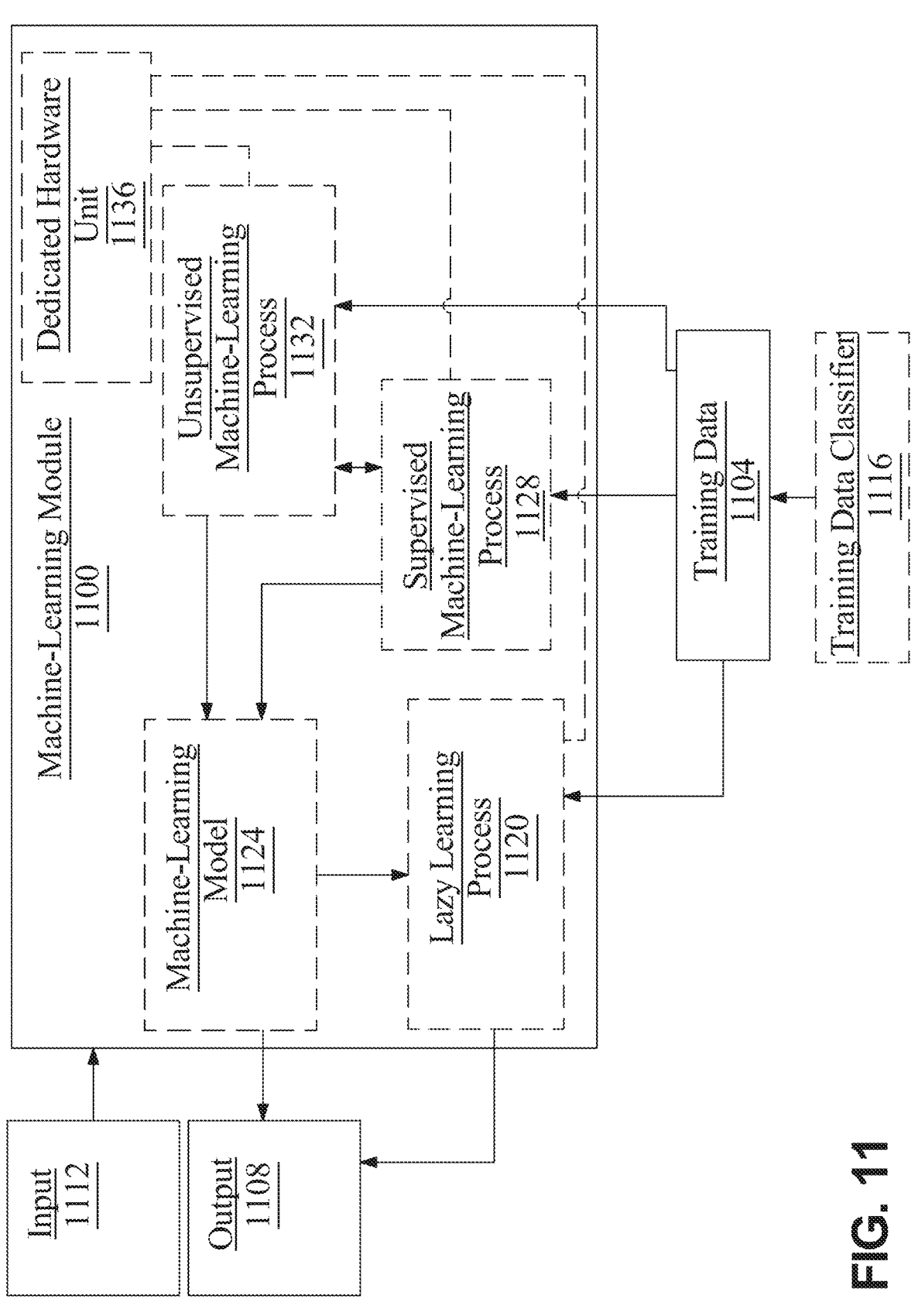
FIG. 11 illustrates a block diagram of an exemplary machine-learning module.

Referring now to FIG. 11, an exemplary embodiment of a machine-learning module 1100 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that auto-matedly uses training data 1104 to generate an algorithm instantiated in hardware or software logic, data structures, and/or functions that will be performed by a computing device/module to produce outputs 1108 given data provided as inputs 1112; this is in contrast to a non-machine learning software program where the commands to be executed are determined in advance by a user and written in a program-ming language.

Still referring to FIG. 11, "training data," as used herein, is data containing correlations that a machine-learning pro-cess may use to model relationships between two or more categories of data elements. For instance, and without limi-tation, training data 1104 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 1104 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 1104 according to various correlations; correlations may indicate causative and/or predictive links between categories of data elements, which may be modeled as relationships such as mathematical relationships by machine-learning processes as described in further detail below. Training data 1104 may be formatted and/or organized by categories of data elements, for instance by associating data elements with one or more descriptors corresponding to categories of data elements. As a non-limiting example, training data 1104 may include data entered in standardized forms by persons or processes, such that entry of a given data element in a given field in a form may be mapped to one or more descriptors of categories. Elements in training data 1104 may be linked to descriptors of categories by tags, tokens, or other data elements; for instance, and without limitation, training data 1104 may be provided in fixed-length formats, formats linking positions of data to categories such as comma-separated value (CSV) formats and/or self-describing for-mats such as extensible markup language (XML), JavaScript Object Notation (JSON), or the like, enabling processes or devices to detect categories of data.

Alternatively or additionally, and continuing to refer to FIG. 11, training data 1104 may include one or more elements that are not categorized; that is, training data 1104 may not be formatted or contain descriptors for some elements of data. Machine-learning algorithms and/or other processes may sort training data 1104 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 1104 to be made applicable for two or more distinct machine-learning algorithms as described in further detail below. Training data 1104 used by machine-learning module 1100 may correlate any input data as described in this disclosure to any output data as described in this disclosure. As a non-limiting illustrative example, input data may include first form data, second form data, data pair, paired data set, and the like. As a non-limiting illustrative example, output data may include first output, second output, paired output, and the like.

Further referring to FIG. 11, training data may be filtered, sorted, and/or selected using one or more supervised and/or unsupervised machine-learning processes and/or models as described in further detail below; such models may include without limitation a training data classifier 1116. Training data classifier 1116 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 1100 may generate a classifier using a classification algorithm, defined as a processes whereby a computing device and/or any module and/or component operating thereon derives a classifier from training data 1104. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 1116 may classify elements of training data to cohorts related to data forms or modalities. As a non-limiting example, training data classifier 1116 may classify elements of training data to cohorts related to a subject or phenomenon.

Still referring to FIG. 11, computing device may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A)$ $P(A)+P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device may then calculate a likelihood table by calculating probabilities of different data entries and classification labels. Computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 11, computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 11, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 11, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 11, computer, processor, and/or module may be configured to preprocess training data. "Preprocessing" training data, as used in this disclosure, is transforming training data from raw form to a format that can be used for training a machine-learning model. Preprocessing may include sanitizing, feature selection, feature scaling, data augmentation and the like.

Still referring to FIG. 11, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 11, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 11, computing device, processor, and/or module may be configured to precondition one or more training examples. For instance, and without limitation, where a machine-learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine-learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine-learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 11, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 11, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 11, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max} : X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation $\sigma$ of a set or subset of values:

$$X_{new} = \frac{X - X_{mean}}{\sigma}.$$

Scaling may be performed using a median value of a a set or subset $X_{median}$ and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 11, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 11, machine-learning module 1100 may be configured to perform a lazy-learning process 1120 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 1104. Heuristic may include selecting some number of highest-ranking associations and/or training data 1104 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 11, machine-learning processes as described in this disclosure may be used to generate machine-learning models 1124. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 1124 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 1124 may be generated by creating an artificial neural network, such as a convolutional neural network comprising an input layer of nodes, one or more intermediate layers, and an output layer of nodes. Connections between nodes may be created via the process of "training" the network, in which elements from a training data 1104 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 11, machine-learning algorithms may include at least a supervised machine-learning process 1128. At least a supervised machine-learning process 1128, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include first form data, second form data, data pair, paired data set, and the like as described above as inputs, first output, second output, paired output, and the like as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 1104. Persons skilled in the art, upon reviewing the entirety of this disclosure, will be aware of various possible variations of at least a supervised machine-learning process 1128 that may be used to determine relation between inputs and outputs. Supervised machine-learning processes may include classification algorithms as defined above.

With further reference to FIG. 11, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 11, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 11, machine learning processes may include at least an unsupervised machine-learning processes 1132. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 1132 may not require a response variable; unsupervised processes 1132 may be used to find interesting patterns and/or inferences between variables, to determine a degree of correlation between two or more variables, or the like.

Still referring to FIG. 11, machine-learning module 1100 may be designed and configured to create a machine-learning model 1124 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 11, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 11, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 11, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 11, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 11, one or more processes or algorithms described above may be performed by at least a dedicated hardware unit 1136. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 1136 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 1136 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 1136 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 12:
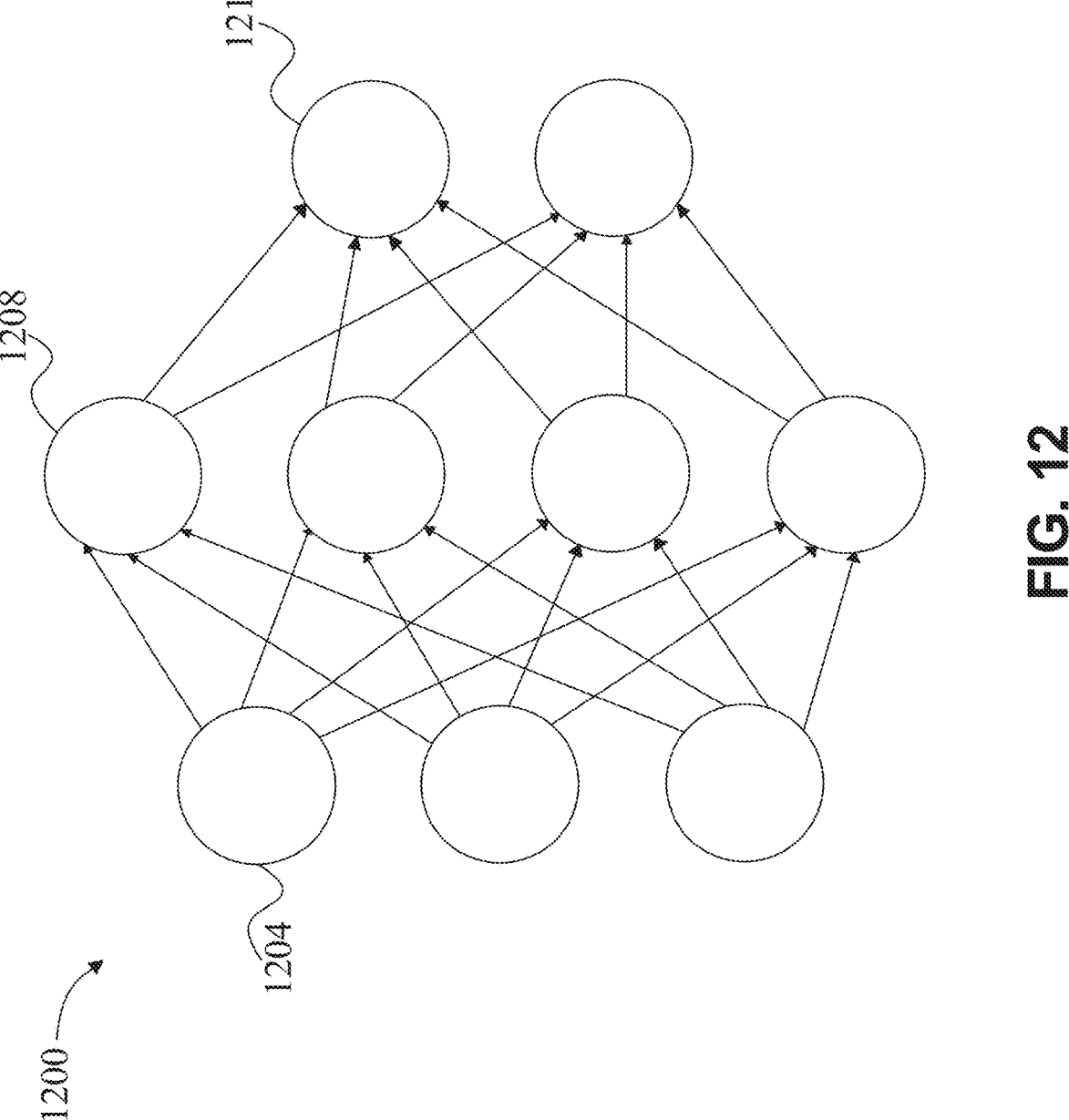
FIG. 12 illustrates a diagram of an exemplary neural network.

Referring now to FIG. 12, an exemplary embodiment of neural network 1200 is illustrated. A neural network 1200 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 1204, one or more intermediate layers 1208, and an output layer of nodes 1212. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 13:
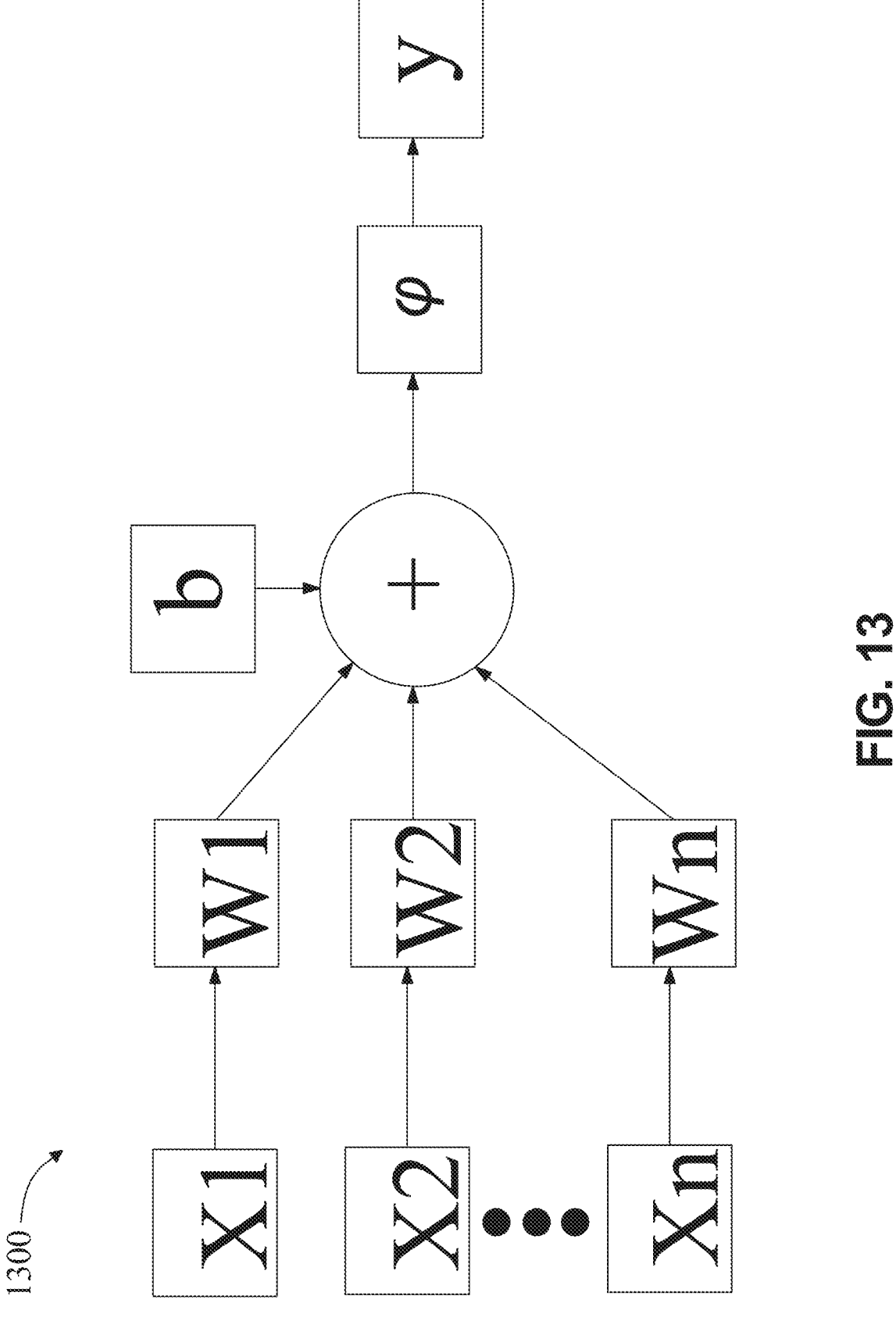
FIG. 13 illustrates a block diagram of an exemplary node in a neural network.

Referring now to FIG. 13, an exemplary embodiment of a node 1300 of a neural network is illustrated. A node may include, without limitation a plurality of inputs xi that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as $f(x) = \tan h^2(x)$, a rectified linear unit function such as $f(x) = \max(0, x)$, a "leaky" and/or "parametric" rectified linear unit function such as $f(x) = \max(ax, x)$ for some a, an exponential linear units function such as $$f(x) = \begin{cases} x & \text{for } x \geq 0 \\ \alpha(e^x - 1) & \text{for } x < 0 \end{cases}$$

for some value of a (this function may be replaced and/or weighted by its own derivative in some embodiments), a softmax function such as $$f(x_i) = \frac{e^x}{\sum_i x_i}$$

where the inputs to an instant layer are xi, a swish function such as $f(x) = x*\text{sigmoid}(x)$, a Gaussian error linear unit function such as $f(x) = a(1 + \tanh(2/w(x + bx^r)))$ for some values of a, b, and r, and/or a scaled exponential linear unit function such as $$f(x) = \lambda \begin{cases} \alpha(e^x - 1) & \text{for } x < 0 \\ x & \text{for } x \geq 0 \end{cases}.$$

Fundamentally, there is no limit to the nature of functions of inputs xi that may be used as activation functions. As a non-limiting and illustrative example, node may perform a weighted sum of inputs using weights $w_i$ that are multiplied by respective inputs xi. Additionally or alternatively, a bias b may be added to the weighted sum of the inputs such that an offset is added to each unit in the neural network layer that is independent of the input to the layer. The weighted sum may then be input into a function p, which may generate one or more outputs y. Weight $w_i$ applied to an input xi may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Referring now to FIG. 14, a flow diagram of an exemplary method 1400 for improving functioning of a validated machine-learning model is illustrated. Method 1400 contains a step 1405 of receiving, using a processor, a validated machine-learning model that has been trained on a validated training set including historical first form data correlated to historical ground truth data, wherein the validated machine-learning model includes a first form accuracy metric. In some embodiments, the first form accuracy metric may be form specific, wherein the first form accuracy metric may be reflective of model accuracy when the first form data in a particular data form is input into the validated machine-learning model. In some embodiments, the first form accuracy metric may include one or both of sensitivity and specificity. In some embodiments, the validated machine-learning model may include a software as a medical device (SaMD). These may be implemented as reference to FIGS. 1-13.

With continued reference to FIG. 14, method 1400 contains a step 1410 of receiving, using a processor, a paired data set including a plurality of data pairs of first form data paired with second form data. In some embodiments, receiving the paired data set may include transforming the first form data in a first data form into a second data form as a function of a transformation model. In some embodiments, the first form data and the second form data may include ECG data. These may be implemented as reference to FIGS. 1-13.

With continued reference to FIG. 14, method 1400 contains a step 1415 of inputting, using a processor, first form data into a validated machine-learning model for each data pair of a plurality of data pairs. This may be implemented as reference to FIGS. 1-13.

With continued reference to FIG. 14, method 1400 contains a step 1420 of determining, using a processor and a validated machine-learning model, a first output as a function of first form data for each data pair of a plurality of data pairs. This may be implemented as reference to FIGS. 1-14.

With continued reference to FIG. 14, method 1400 contains a step 1425 of inputting, using a processor, second form data into a validated machine-learning model for each data pair of a plurality of data pairs. This may be implemented as reference to FIGS. 1-13.

With continued reference to FIG. 14, method 1400 contains a step 1430 of determining, using a processor and a validated machine-learning model, a second output as a function of second form data for each data pair of a plurality of data pairs. This may be implemented as reference to FIGS. 1-14.

With continued reference to FIG. 14, method 1400 contains a step 1435 of pairing, using a processor, a first output and a second output as a paired output for each data pair of a plurality of data pairs. In some embodiments, the first output and the second output may indicate a diagnosis based on the first form data and the second form data respectively. These may be implemented as reference to FIGS. 1-13.

With continued reference to FIG. 14, method 1400 contains a step 1440 of comparing, using a processor, the paired output by comparing the first output to the second output. This may be implemented as reference to FIGS. 1-13.

With continued reference to FIG. 14, method 1400 contains a step 1445 of determining, using a processor, that a second form accuracy metric exceeds an accuracy threshold as a function of the comparison of the paired output for each data pair of the plurality of data pairs and the first form accuracy metric. In some embodiments, determining that the second form accuracy metric exceeds the accuracy threshold may include generating a confidence score for each data pair of the plurality of data pairs and determining that the second form accuracy metric exceeds the accuracy threshold as a function of the confidence score. In some embodiments, determining that the second form accuracy metric exceeds the accuracy threshold may include generating a confidence score as a function of closeness of the paired output to the accuracy threshold, wherein the confidence score may include a positive classification and a negative classification. In some embodiments, determining that the second form accuracy metric exceeds the accuracy threshold may include adding correlations between the second form data and the second output to the validated training set as a function of the second form accuracy metric. These may be implemented as reference to FIGS. 1-13.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 15:
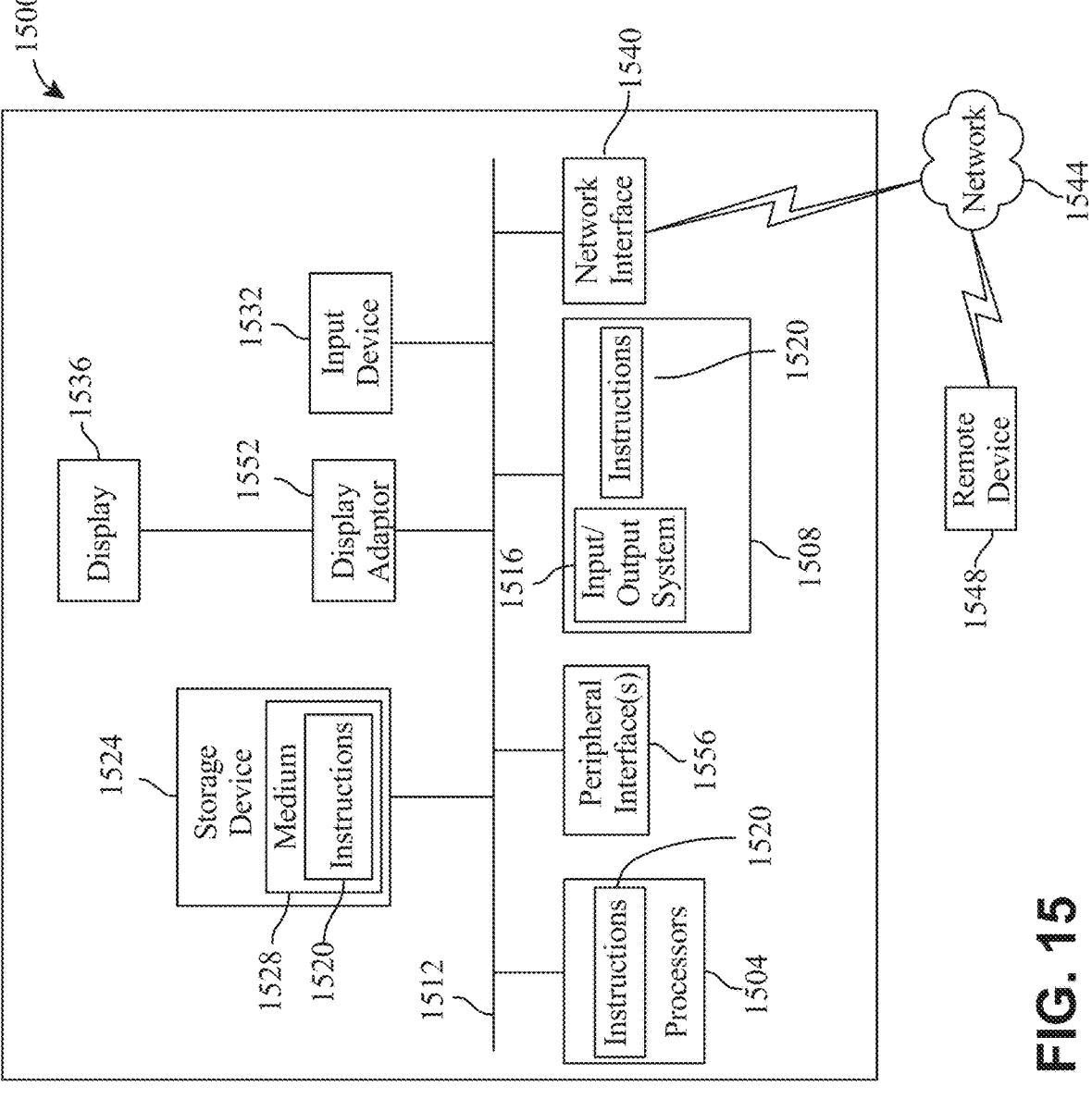
FIG. 15 illustrates a block diagram of a computing system that can be used to implement any one or more of the methodologies disclosed herein and any one or more portions thereof. The drawings are not necessarily to scale and may be illustrated by phantom lines, diagrammatic representations and fragmentary views. In certain instances, details that are not necessary for an understanding of the embodiments or that render other details difficult to perceive may have been omitted.

FIG. 15 shows a diagrammatic representation of one embodiment of a computing device in the exemplary form of a computer system 1500 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1500 includes a processor 1504 and memory 1508 that communicate with each other, and with other components, via a bus 1512. Bus 1512 may include any of several types of bus structures including, but not limited to, memory bus, a memory controller, a peripheral bus, a local bus, and any combinations thereof, using any of a variety of bus architectures.

Processor 1504 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1504 may be organized according to Von Neumann and/or Harvard architecture as a non-limiting example. Processor 1504 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 1508 may include various components (e.g., machine-readable media) including, but not limited to, a random-access memory component, a read only component, and any combinations thereof. In one example, a basic input/output system 1516 (BIOS), including basic routines that help to transfer information between elements within computer system 1500, such as during start-up, may be stored in memory 1508. Memory 1508 may also include (e.g., stored on one or more machine-readable media) instructions (e.g., software) 1520 embodying any one or more of the aspects and/or methodologies of the present disclosure. In another example, memory 1508 may further include any number of program modules including, but not limited to, an operating system, one or more application programs, other program modules, program data, and any combinations thereof.

Computer system 1500 may also include a storage device 1524. Examples of a storage device (e.g., storage device 1524) include, but are not limited to, a hard disk drive, a magnetic disk drive, an optical disc drive in combination with an optical medium, a solid-state memory device, and any combinations thereof. Storage device 1524 may be connected to bus 1512 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1524 (or one or more components thereof) may be removably interfaced with computer system 1500 (e.g., via an external port connector (not shown)). Particularly, storage device 1524 and an associated machine-readable medium 1528 may provide nonvolatile and/or volatile storage of machine-readable instructions, data structures, program modules, and/or other data for computer system 1500. In one example, software 1520 may reside, completely or partially, within machine-readable medium 1528. In another example, software 1520 may reside, completely or partially, within processor 1504.

Computer system 1500 may also include an input device 1532. In one example, a user of computer system 1500 may enter commands and/or other information into computer system 1500 via input device 1532. Examples of an input device 1532 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1532 may be interfaced to bus 1512 via any of a variety of interfaces (not shown) including, but not limited to, a serial interface, a parallel interface, a game port, a USB interface, a FIRE-WIRE interface, a direct interface to bus 1512, and any combinations thereof. Input device 1532 may include a touch screen interface that may be a part of or separate from display 1536, discussed further below. Input device 1532 may be utilized as a user selection device for selecting one or more graphical representations in a graphical interface as described above.

A user may also input commands and/or other information to computer system 1500 via storage device 1524 (e.g., a removable disk drive, a flash drive, etc.) and/or network interface device 1540. A network interface device, such as network interface device 1540, may be utilized for connecting computer system 1500 to one or more of a variety of networks, such as network 1544, and one or more remote devices 1548 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1544, may employ a wired and/or a wireless mode of communication. In general, any network topology may be used. Information (e.g., data, software 1520, etc.) may be communicated to and/or from computer system 1500 via network interface device 1540.

Computer system 1500 may further include a video display adapter 1552 for communicating a displayable image to a display device, such as display 1536. Examples of a display device include, but are not limited to, a liquid crystal display (LCD), a cathode ray tube (CRT), a plasma display, a light emitting diode (LED) display, and any combinations thereof. Display adapter 1552 and display 1536 may be utilized in combination with processor 1504 to provide graphical representations of aspects of the present disclosure. In addition to a display device, computer system 1500 may include one or more other peripheral output devices including, but not limited to, an audio speaker, a printer, and any combinations thereof. Such peripheral output devices may be connected to bus 1512 via a peripheral interface 1556. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods and apparatuses according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for improving functioning of a validated machine-learning model, the apparatus comprising:

a computing device comprising a processor and a memory, the memory containing instructions that, when run, configure the processor to:

receive a validated machine-learning model that has been trained on a validated training set comprising historical first form data correlated to historical ground truth data, wherein the validated machine-learning model comprises a first form accuracy metric;

receive a paired data set comprising a plurality of data pairs of first form data paired with second form data, wherein the first form data comprises real-time electrocardiogram (ECG) data and wherein receiving the paired data set comprises transforming the first form data in a first data form into a second data form as a function of a transformation model which includes a signal conversion model trained with training data comprising known electrical anomalies correlated to desired channel selections;

for each data pair of the plurality of data pairs:

input the first form data into the validated machine-learning model;

determine, using the validated machine-learning model, a first output as a function of the first form data;

input the second form data into the validated machine-learning model;

determine, using the validated machine-learning model, a second output as a function of the second form data;

pair the first output and the second output as a paired output; and compare the paired output by comparing the first output to the second output, wherein comparing the first output to the second output comprises deriving a second form accuracy metric; and determine whether the second form accuracy metric exceeds an accuracy threshold as a function of the comparison of the paired output for each data pair of the plurality of data pairs and the first form accuracy metric.

2. The apparatus of claim 1, wherein the first form accuracy metric is form specific, wherein the first form accuracy metric is reflective of model accuracy when the first form data in a particular data form is input into the validated machine-learning model.

3. The apparatus of claim 1, wherein the first form accuracy metric comprises one or more of sensitivity and specificity.

4. The apparatus of claim 1, wherein the validated machine-learning model comprises a software as a medical device (SaMD).

5. The apparatus of claim 1, wherein determining whether the second form accuracy metric exceeds the accuracy threshold comprises:

generating a confidence score for each data pair of the plurality of data pairs; and determining whether the second form accuracy metric exceeds the accuracy threshold as a function of the confidence score.

6. The apparatus of claim 1, wherein determining whether the second form accuracy metric exceeds the accuracy threshold comprises generating a confidence score as a function of closeness of the paired output to the accuracy threshold, wherein the confidence score comprises one of a positive classification and a negative classification.

7. The apparatus of claim 1, wherein determining whether the second form accuracy metric exceeds the accuracy threshold comprises adding correlations between the second form data and the second output to the validated training set as a function of the second form accuracy metric.

8. The apparatus of claim 1, wherein the first output and the second output indicates a diagnosis based on the first form data and the second form data respectively.

9. A method for improving functioning of a validated machine-learning model, the method comprising:

receiving, using a processor, a validated machine-learning model that has been trained on a validated training set comprising historical first form data correlated to historical ground truth data, wherein the validated machine-learning model comprises a first form accuracy metric;

receiving, using the processor, a paired data set comprising a plurality of data pairs of first form data paired with second form data, wherein the first form data comprises real-time electrocardiogram (ECG) data and wherein receiving the paired data set comprises transforming the first form data in a first data form into a second data form as a function of a transformation model which includes a signal conversion model trained with training data comprising known electrical anomalies correlated to desired channel selections;

inputting, using the processor, the first form data into the validated machine-learning model for each data pair of the plurality of data pairs;

determining, using the processor and the validated machine-learning model, a first output as a function of the first form data for each data pair of the plurality of data pairs;

inputting, using the processor, the second form data into the validated machine-learning model for each data pair of the plurality of data pairs;

determining, using the processor and the validated machine-learning model, a second output as a function of the second form data for each data pair of the plurality of data pairs;

pairing, using the processor, the first output and the second output as a paired output for each data pair of the plurality of data pairs;

comparing, using the processor, the paired output by comparing the first output to the second output, wherein comparing the first output to the second output comprises deriving a second form accuracy metric; and determining, using the processor, whether the second form accuracy metric exceeds an accuracy threshold as a function of the comparison of the paired output for each data pair of the plurality of data pairs and the first form accuracy metric.

10. The method of claim 9, wherein the first form accuracy metric is form specific, wherein the first form accuracy metric is reflective of model accuracy when the first form data in a particular data form is input into the validated machine-learning model.

11. The method of claim 9, wherein the first form accuracy metric comprises one or more of sensitivity and specificity.

12. The method of claim 9, wherein the validated machine-learning model comprises a software as a medical device (SaMD).

13. The method of claim 9, wherein determining whether the second form accuracy metric exceeds the accuracy threshold comprises:

generating a confidence score for each data pair of the plurality of data pairs; and determining that the second form accuracy metric exceeds the accuracy threshold as a function of the confidence score.

14. The method of claim 9, wherein determining whether the second form accuracy metric exceeds the accuracy threshold comprises generating a confidence score as a function of closeness of the paired output to the accuracy threshold, wherein the confidence score comprises one of a positive classification and a negative classification.

15. The method of claim 9, wherein determining whether the second form accuracy metric exceeds the accuracy threshold comprises adding correlations between the second form data and the second output to the validated training set as a function of the second form accuracy metric.

16. The method of claim 9, wherein the first output and the second output indicates a diagnosis based on the first form data and the second form data respectively.

* * * * *